United States Patent
Chen et al.

(10) Patent No.: US 9,603,582 B2
(45) Date of Patent: Mar. 28, 2017

(54) CONTRAST ASSISTED INTRAVASCULAR ULTRASOUND IMAGING

(75) Inventors: Xucai Chen, Pittsburgh, PA (US);
Francois T. H. Yu, Pittsburgh, PA (US);
Flordeliza S. Villanueva, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 144 days.

(21) Appl. No.: 14/241,051

(22) PCT Filed: Aug. 24, 2012

(86) PCT No.: PCT/US2012/052373
§ 371 (c)(1),
(2), (4) Date: Feb. 25, 2014

(87) PCT Pub. No.: WO2013/032946
PCT Pub. Date: Mar. 7, 2013

(65) Prior Publication Data
US 2014/0236005 A1    Aug. 21, 2014

Related U.S. Application Data

(60) Provisional application No. 61/528,099, filed on Aug. 26, 2011.

(51) Int. Cl.
*A61B 8/00* (2006.01)
*A61B 8/12* (2006.01)
*A61K 49/22* (2006.01)
*A61M 31/00* (2006.01)
(Continued)

(52) U.S. Cl.
CPC .......... *A61B 8/4488* (2013.01); *A61B 8/0891* (2013.01); *A61B 8/12* (2013.01); *A61B 8/481* (2013.01); *A61B 8/5246* (2013.01); *A61K 49/223* (2013.01); *A61B 8/0883* (2013.01); *A61B 8/4494* (2013.01); *A61B 8/461* (2013.01);
(Continued)

(58) Field of Classification Search
CPC ..... A61B 8/4488; A61B 8/481; A61B 8/0891; A61B 8/5246; A61B 8/12; A61B 8/4494; A61B 8/461; A61B 8/0883; A61K 49/223; G01S 7/52022; A61M 31/005
USPC .................................................. 600/437–469
See application file for complete search history.

(56) References Cited

U.S. PATENT DOCUMENTS 6,726,629 B1 *   4/2004   Frinking ................ A61B 8/481
                                                                600/437
6,752,762 B1 *   6/2004   DeJong .................. A61B 8/481
                                                                600/458
(Continued)

*Primary Examiner* — Sanjay Cattungal
(74) *Attorney, Agent, or Firm* — Klarquist Sparkman, LLP

(57) ABSTRACT

A method of imaging a blood vessel includes delivering a bubble-based contrast agent within the vessel and positioning at least one ultrasound device in the vicinity of the bubble-based contrast agent within the vessel. A first burst of low-frequency ultrasound energy can be delivered to excite the bubble-based contrast agent into oscillation within the vessel, and a second burst of high-frequency ultrasound energy can be delivered at the excited bubble-based contrast agent. A return signal from the burst of high-frequency ultrasound energy can be received and processed to obtain one or more images.

18 Claims, 20 Drawing Sheets

(51) Int. Cl.
*A61B 8/08* (2006.01)
*G01S 7/52* (2006.01)
(52) U.S. Cl.
CPC ........ *A61M 31/005* (2013.01); *G01S 7/52022* (2013.01)

(56) References Cited

U.S. PATENT DOCUMENTS

| | | | |
|---|---|---|---|
| 7,621,873 B2* | 11/2009 | Owen | A61B 8/00 310/311 |
| 2001/0021809 A1* | 9/2001 | De Jong | B06B 1/0614 600/458 |
| 2002/0129656 A1* | 9/2002 | Tsuzuki | G01S 7/52038 73/620 |
| 2006/0079773 A1 | 4/2006 | Mourad et al. | |
| 2010/0331686 A1* | 12/2010 | Hossack | A61B 17/2202 600/439 |
| 2011/0144494 A1* | 6/2011 | Mehi | B06B 1/0622 600/441 |

* cited by examiner

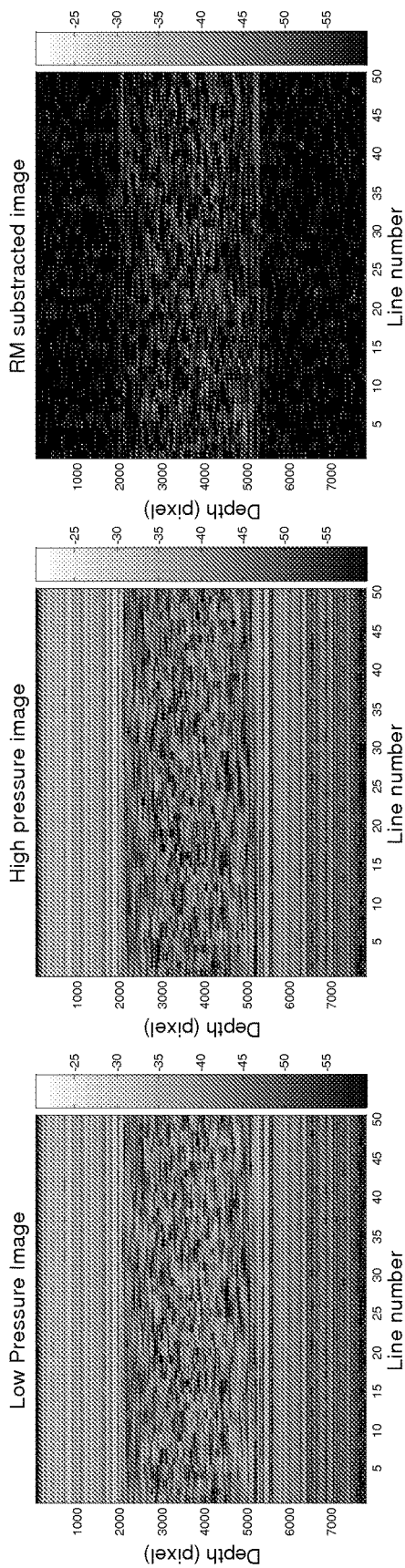
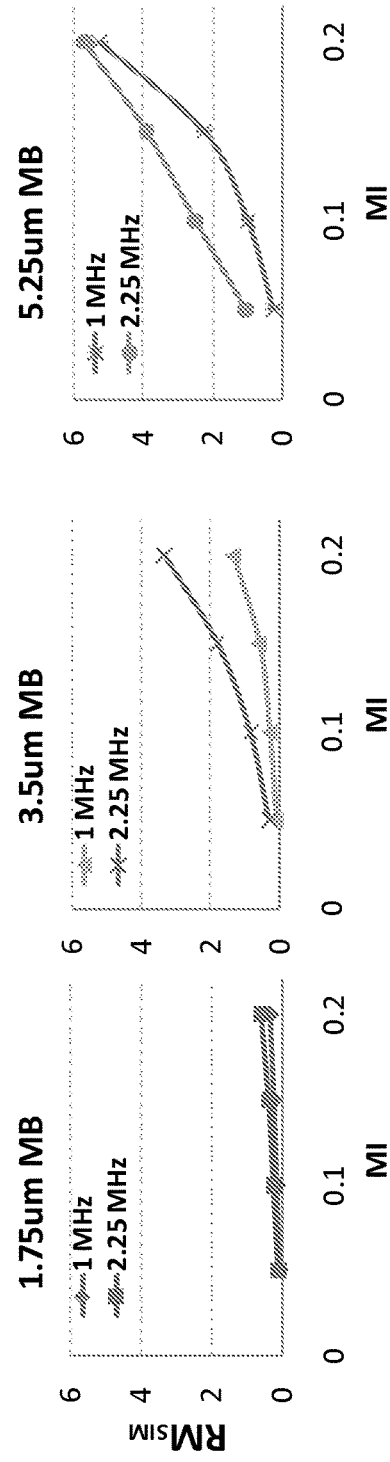
FIG. 4
FIG. 5

B-mode    RM-mode

CONTRAST ASSISTED INTRAVASCULAR ULTRASOUND IMAGING

CROSS REFERENCE TO RELATED APPLICATIONS

This is the U.S. National Stage of International Application No. PCT/US2012/052373, filed Aug. 24, 2012, which was published in English under PCT Article 21(2), which in turn claims the benefit of U.S. Provisional Application No. 61/528,099, filed Aug. 26, 2011. The provisional application is incorporated herein in its entirety.

FIELD

This disclosure is directed to methods and apparatuses for performing contrast assisted intravascular ultrasound imaging.

BACKGROUND

In patients with coronary artery disease, acute coronary syndromes can account for up to 70% of deaths. The progression of an asymptomatic fibroatheromatous plaque into a vulnerable plaque is often poorly diagnosed and not generally well understood. In many instances, the lesions responsible for acute coronary syndromes are not flow-limiting on coronary angiography and, as a result, current imaging technologies are not able to sufficiently identify patients at greatest risk for future acute coronary syndromes.

Higher resolution requirements for coronary imaging have driven the development of catheter based technologies, which can permit examination of physical features of vulnerable plaques, such as plaque morphology (large necrotic core and thin fibrous cap, using optical coherence tomography and intravascular ultrasound (IVUS)), mechanical properties (palpography and intravascular elastography using IVUS), composition (Virtual histology), or lipid content (near-infrared spectroscopy). However, conventional approaches for coronary imaging have significant shortcomings and improvements to the current capabilities in detecting vulnerable plaque and understanding plaque progression in the coronaries is desirable.

SUMMARY

In one embodiment, a method of imaging a blood vessel is provided. The method includes delivering a bubble-based contrast agent within the vessel and positioning at least one ultrasound device in the vicinity of the bubble-based contrast agent within the vessel. A first burst of ultrasound energy is delivered, with the first burst of energy comprising a first low-frequency component and a first high-frequency component directed at the bubble-based contrast agent to excite the bubble-based contrast agent. The first high-frequency component and the first low-frequency component can have a first relative timing. A second burst of ultrasound energy is delivered, with the second burst of energy comprising a second low-frequency component and a second high-frequency component directed at the excited bubble-based contrast agent. The second high-frequency component and the second low-frequency component can have a second relative timing. One or more return signals can be received from the high-frequency ultrasound energy of the first and second bursts and the one or more return signals can be processed to obtain a first image of the excited bubble-based contrast agent. The first and second relative timings can be different.

In another embodiment, an apparatus for imaging a blood vessel is provided. The catheter can include an elongate shaft having a distal end portion and a delivery device for delivering a bubble-based contrast agent into the vessel. At least one ultrasound device can be coupled to the distal end portion of the elongate shaft, with the ultrasound device being configured to deliver first bursts of low-frequency and high-frequency ultrasound energy, and second bursts of low-frequency and high-frequency ultrasound energy at the bubble-based contrast agent after it has been delivered into the vessel. A processor can be configured to control the delivery of the first and second bursts, with the processor being configured to control the relative timing of the low-frequency and high-frequency ultrasound energy of the respective first and second bursts. An image processing device is capable of receiving returned signals from the first and second bursts and can be configured to generate one or more images corresponding to the returned signals.

The foregoing and other objects, features, and advantages of the invention will become more apparent from the following detailed description, which proceeds with reference to the accompanying figures.

BRIEF DESCRIPTION OF THE DRAWINGS

FIG. 4 illustrates a typical acquisition for M-mode images of low pressure, high pressure, and RM for 50 line pairs.

FIG. 5 illustrates a simulation of RM based on monopole scattering theory and thin layer microbubble for mean, small and large MB present in studied MB suspension.

DETAILED DESCRIPTION

Figure 1:
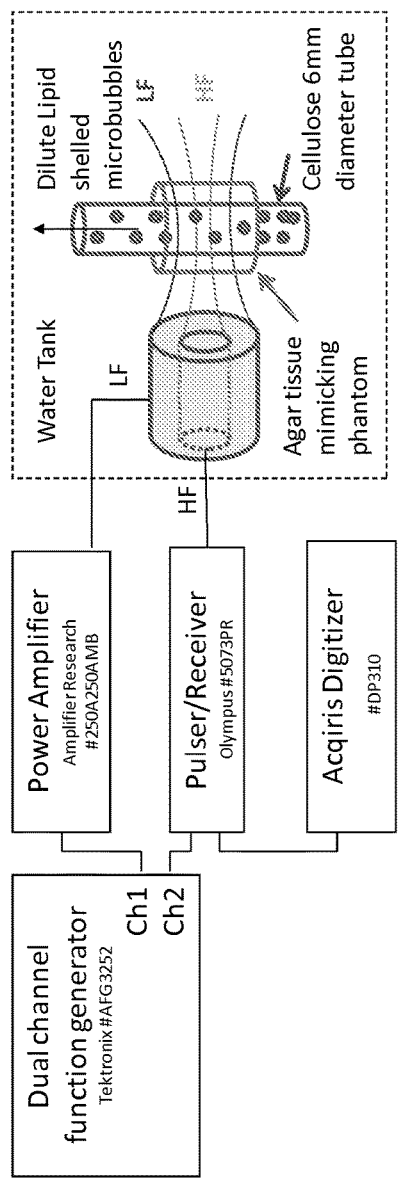
FIG. 1 illustrates an exemplary system for providing contrast assisted ultrasound imaging.

The following description is exemplary in nature and is not intended to limit the scope, applicability, or configuration of the invention in any way. Various changes to the described embodiment may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." As used herein, the term "catheter" refers to any elongate flexible structure that defines a lumen and which can be inserted into the body of a subject. As used herein, the term "low frequency" or "LF" means a frequency of less than 5 MHz and the term "high frequency" or "HF" means a frequency of greater than 15 MHz.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Moreover, for the sake of simplicity, the attached figures may not show the various ways (readily discernable, based on this disclosure, by one of ordinary skill in the art) in which the disclosed methods and apparatuses can be used in combination with other methods and apparatuses. Additionally, the description sometimes uses terms such as "produce" and "provide" to describe the disclosed method. These terms are high-level abstractions of the actual operations that can be performed. The actual operations that correspond to these terms can vary depending on the particular implementation and are, based on this disclosure, readily discernible by one of ordinary skill in the art.

Radial Modulation Imaging

Lipid-encapsulated perfluorocarbon microbubbles (MB) are ultrasound contrast agents that have been originally developed to enhance blood echogenicity. They are used in a wide range of diagnostic applications including the study of left ventricular function and myocardial perfusion. These gaseous microbubbles introduce a strong contrast in compressibility at the gas/liquid interface, strongly scattering the impinging ultrasound wave and producing a hyperechogenic signal. In some embodiments, microbubbles can be made to oscillate non-linearly, thus permitting microbubble specific imaging, using several strategies including harmonics, sub-harmonic, ultra-harmonic and pulse inversion. These approaches can enhance MB signal while decreasing signal from surrounding tissues.

For a free bubble, the Minnaert resonance frequency is related to the bubble diameter (d) by $F=6/d$, where F is the frequency. The synthesis of stable submicron-sized bubble as required for imaging at 20-50 MHz remains challenging. Because commercial lipid microbubbles are generally found in the 1-6 µm size range, new strategies for imaging >1 µm sized microbubbles for high frequency applications are desirable. The embodiments disclosed herein provide methods and systems that utilize radial modulation (RM) to address the shortcomings in conventional techniques and methods.

RM is a dual frequency technique in which a low frequency, also called modulation frequency, is used to manipulate the microbubble radius, while high frequency scattering variations are monitored. One implementation of this approach includes synchronizing two successive high frequency (HF) pulses such that they reach the microbubble, respectively, in a compressed and an expanded state induced by the low frequency (LF) pressure wave. Subtracting both HF scattered lines theoretically results in an RM signal, in which tissue scattering is suppressed because it is not affected by the LF modulation pulse. The RM signal generally increases with LF amplitude; however, the chosen LF amplitude can ultimately be limited by the appearance of harmonics of the LF in the HF bandwidth when the bubble oscillations become too large. These harmonics, discussed in more detail below, can decrease the image resolution.

For a bubble of particular size, simulation tools can allow prediction of the response of the microbubble and the level of modulation that can be achieved for a typical lipid microbubble, thus predicting the RM contrast at high frequency for a particular low frequency modulation pulse. In practice, however, microbubbles are polydispersed in size and, as a result, it can be difficult to determine ideal modulation pulse frequencies and amplitudes. In the first example discussed herein, radial modulation contrast at a HF of 20 MHz using a lipid shelled microbubble suspension was provided while varying LF modulation pulse amplitude and frequency. LF frequencies were chosen near (2.25 MHz) and below (1 MHz) the mean bubble size resonance frequency. As discussed in more detail below, the influence of frequency and amplitude in the selection of the modulation frequency for radial modulation imaging of a diluted polydispersed MB suspension was analyzed, demonstrating that high resolution imaging of a single bubble can be performed along with substantial tissue cancellation using the radial modulation approaches described herein.

Example 1

The RM contrast can be predicted for a single MB using thin shelled microbubble oscillation theory. The simulation package "Bubblesim" was used to estimate the maximal and minimal radii of MB ranging from 1.75 to 5.25 um when submitted to a 5 cycle LF pulse. For this example, shell viscosity was chosen as 0.8 Pa·s, shear modulus as 50 MPa, shell thickness as 4 nm. The Raleigh-Plesset liquid model with radiation damping coupled to an isothermal gas phase was solved using the stiff variable order solver. The monopole scattering theory for ka~0.3 (k is the wave length and a the scatterer size) predicts a backscattered power that is proportional to the scatterer geometrical cross section. Hence, the RM contrast for a single MB was then estimated as $RM_{SIM} = (Rmax^2 - Rmin^2)/(Rmin^2)$ (eq.1), where R is the simulated bubble radius.

FIG. 1 illustrates the system used in connection with Example 1. Lipid-encapsulated perfluorocarbon MB (3.54±1.76 μm) were measured (Beckham Coulter Multisizer3, Brea, Calif.), diluted to a concentration of 3e5 MB/mL and circulated at a flow rate of 0.5 mL/min in a 6 mm diameter cellulose tube. This flow chamber was surrounded by a hollow 3 mm thick 2% (w/w) agar cylindrical phantom comprising 0.5% (w/w) sigmacell (20 um Sigmacell particles, Sigma-Aldrich, Saint Louis, Mo.) to provide tissue scattering. A 20 MHz single element transducer (0.25 inch/F4, Olympus, Waltham, Mass.) was concentrically housed in the center of hollow 1 MHz and 2.25 MHz transducers (1 inch/F2, Valpey Fisher, Hopkinton, Mass.) and the resulting confocal pressure fields were calibrated with a hydrophone (HGL0200, OndaCorp, Sunnyvale, Calif.).

Figure 2:
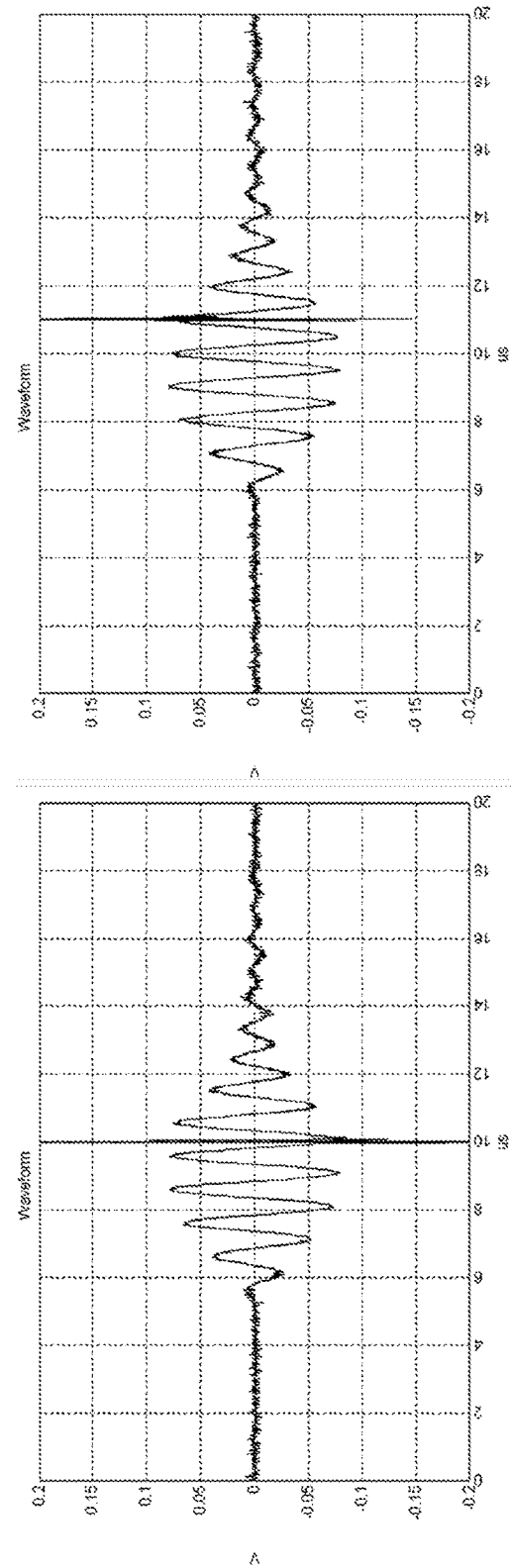
FIG. 2 illustrates a pair of pressure waveforms.
Figure 7A:
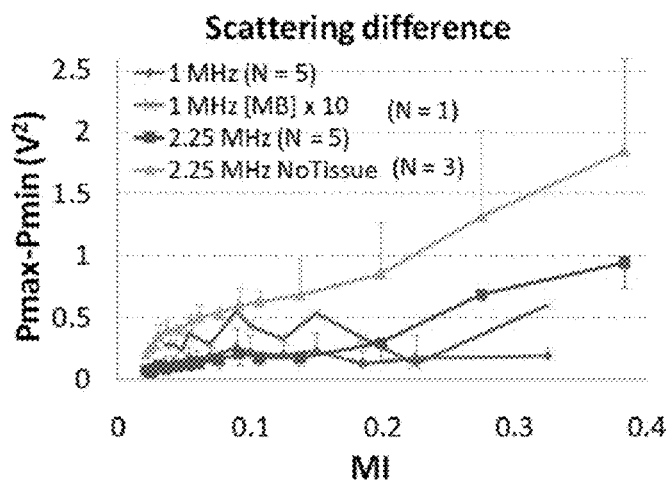
FIG. 7 illustrates (a) scattering difference, (b) RM and (c) LF harmonics as a function of MI for 1 and 2.25 MHz LF, measured at HF=20 MHz. RM is maximal at $0.1<MI<0.150$ for both frequencies.
Figure 7B:
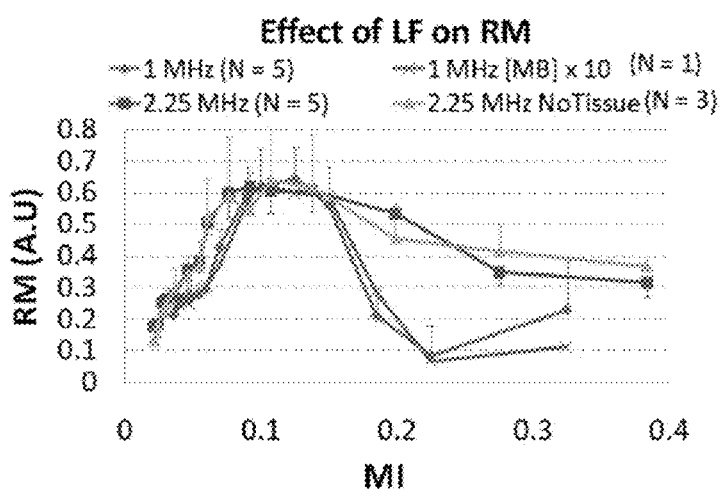

FIG. 2 illustrates a pair of pressure waveforms pulsed at 1 MHz. A similar pulse pair was used at 2.25 MHz. Dual frequency (20/1 MHz combination) pressure waveforms were measured with a hydrophone, with the left panel of FIG. 2 showing imaging HF sent during LF low pressure phase and the right panel of FIG. 2 showing HF sent during LF high pressure phase. The LF and synchronization for the HF were generated by a dual channel function generator (Tektroniks AFG3252), while the HF pulse was sent using an ultrasound pulser/receiver (Panametrics PR5073, Waltham, Mass.). RF signals were digitized at a sampling frequency of 400 MHz (Acqiris DP310, Agilent technologies, Santa Clara, Calif.) and stored for offline processing. During insonation of the circulating MB, 50 independent HF line pairs were recorded while varying LF pressure from 0.02 to 0.4 mechanical index (MI=pressure/$F^{0.5}$). The experimental RM signal was defined as $$RM = \frac{\overline{P_{max}} - \overline{P_{min}}}{\overline{P_{min}}}, \quad (eq. 2)$$

where $\overline{P_{max}}$ and $\overline{P_{min}}$ are respectively the mean backscattered power in the HF bandwidth at maximal and minimal bubble expansion (cf. FIG. 7b). Normalization reduces RM to the mean RM for an equivalent single MB and allows comparison with $RM_{SIM}$.

Figure 3:
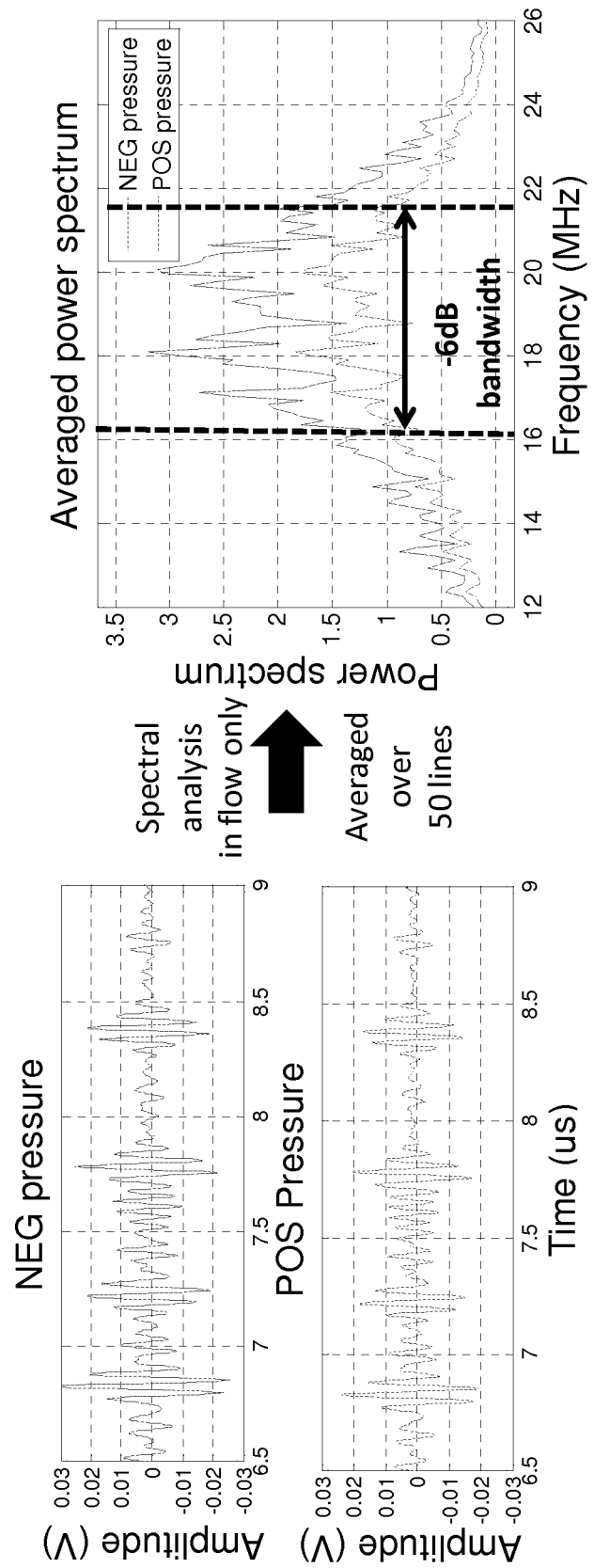
FIG. 3 illustrates an exemplary RF line pair along with the backscatter power spectrum averaged over 50 lines pairs for data corresponding to the MB.

FIG. 3 shows one typical RF line pair (left) along with the backscatter power spectrum averaged over 50 lines pairs for data corresponding to the MB only. FIG. 3 thus illustrates a typical HF RF signal pair for 1 MHz LF, whereby at this frequency low pressure corresponds to maximal expansion. The signal inside the black box corresponds to MB. As shown in FIG. 3, a single MB being modulated by the LF can be discerned within the box as spikes, with first and last portions of the data being signals from the tissue-mimicking phantom. The right panel of FIG. 3 illustrates 50 line pairs that were averaged to compute the experimental RM.

Data for $\overline{P_{max}} - \overline{P_{min}}$ before normalization is also reported in the Example 1—Results section below for comparison with RM (cf. FIG. 7(a)). The presence of LF harmonics was also measured by passively recording the HF without sending a HF pulse (cf. FIG. 7c). Measurements were performed repeated 5 times with the tissue-mimicking phantom at 1 and 2.25 MHz and 3 times without the tissue phantom only at 2.25 MHz. The MB concentration was also increased by a factor of 10 and RM was measured with the attenuation phantom at 1 MHz.

M-mode images were computed by taking the amplitude of the Hilbert transform of individual RF lines. Line pairs were separated into 2 sets of 50 lines images, respectively low and high pressure images. RM images were computed by subtracting the low pressure M-mode image from the high pressure image. FIG. 4 illustrates a typical acquisition for M-mode images of low pressure (left), high pressure (center) and RM for 50 line pairs, with the images being displayed using a 40 dB dynamic range. The upper and lower portions of the images are from the tissue-mimicking phantom, and the central portion indicates flowing MB. Thus, the scatterers in the tissue phantom appear as generally continuous lines whereas flowing MB can be seen in the middle section. In the RM image, tissue signal is cancelled out while MB signal appears. (LF=1 MHz, MI=0.1, delay=5.2 us).

Example 1

Results

In FIG. 5, RM were computed (eq.1) based on simulation for the smaller, mean and larger MB found in the MB suspension used for this study for LF frequencies of 1 and 2.25 MHz. RM increases with MI and with LF for the same MI. Thus, FIG. 5 illustrates a simulation of RM based on monopole scattering theory and thin layer microbubble ("BubbleSim" package) for mean, small and large MB present in studied MB suspension. The asterisks shown in FIG. 5 indicate the presence of non-linear oscillations. As shown in FIG. 5, increasing the bubble size also increases RM.

Figure 6:
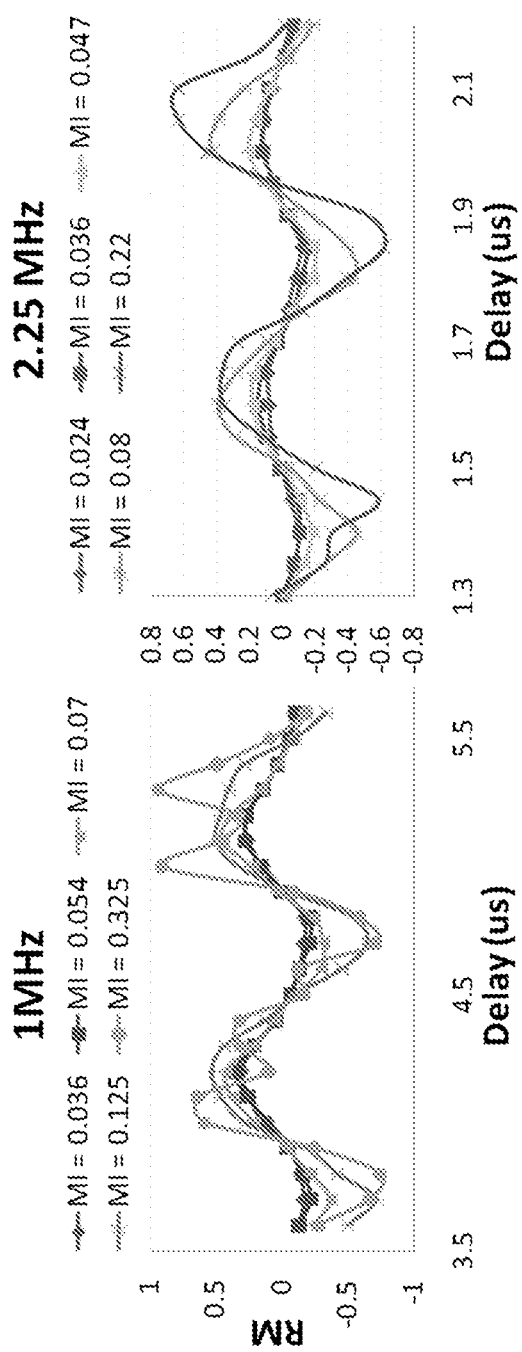
FIG. 6 illustrates RM as a function of increasing delay between LF and HF pulses shown in FIG. 2.

Phase Variations:

To determine optimal signal synchronizations, the delay was first varied between LF and HF pulses. FIG. 6 illustrates RM as a function of increasing delay between LF and HF pulses shown in FIG. 2. Both HF pulses are moved in pair along the LF by changing the delay. For MI<0.1, bubble oscillations are in the linear regime and changing the synchronization induced sinusoidal variations of RM at LF for about MI<0.125. In this range, increasing the pressure increased RM. For MI>0.125, some distortion appeared in RM, either as oscillations at higher frequency (1 MHz data), or as a variation in the phase (2.25 MHz data).

In the linear oscillation regime (MI<0.125), the maxima correspond to a synchronization setup when the HF successively reached the MB at maximal difference between expanded and compressed states. Conversely, the minima correspond to a pair of HF reaching the MB first in a compressed and then an expanded state. Also, the minima in RM were found to be in phase with the maxima in LF pressure at 1 MHz, and delayed by π/2 for 2.25 MHz, corresponding with theoretical predictions for a damped first order linear oscillator. For the following results, the delay was chosen so that RM was positive and maximal.

Figure 7C:
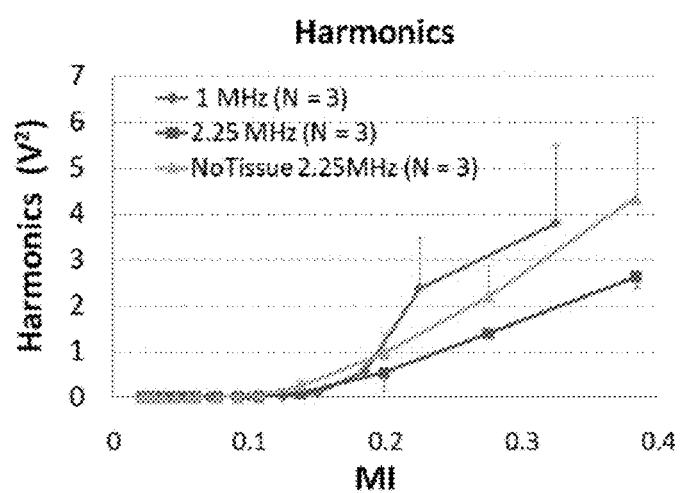

LF Amplitude, Tissue Attenuation and Normalization:

FIG. 7 illustrates (a) scattering difference, (b) RM and (c) LF harmonics as a function of MI for 1 and 2.25 MHz LF, measured at HF=20 MHz. RM is maximal at 0.1<MI<0.150 for both frequencies. LF harmonics in the HF bandwidth appear at MI>0.15. In FIG. 7a, $\overline{P_{MAX}}$-$\overline{P_{MIN}}$ data are plotted as a function of LF MI, at 1 MHz at nominal and high (10 times) MB concentration with the tissue phantom, and at 2.25 MHz at nominal concentration with and without the tissue phantom. As shown in FIG. 7, the power difference generally increases with MI and MB concentration, while it decreases with tissue attenuation. Oscillations can be seen in the high concentration curve, because of MB floatation between successive acquisitions. This effect was less apparent for the other data sets because of lower concentration and averaging over more repetitions. In FIG. 7b, the scattering power difference was normalized by $\overline{P_{MIN}}$. All curves display similar trends: RM first increases with MI, stabilizes at a plateau around 60% at 0.1<MI<0.15 and decreases for higher MI. For MI<0.1, 2.25 MHz produced more RM than 1 MHz for the same MI. However, the maximal RM amplitude at the plateau was similar. In FIG. 7c, the LF harmonics power appearing in the HF bandwidth is plotted as a function of the MI. These data were obtained while the HF was turned off. It was observed that the LF harmonics appear for MI>0.15 at both frequencies, concomitantly with the RM decrease in FIG. 7b.

The normalization step for RM had many advantages. First, it corrected for MB concentration differences between acquisitions, as can be seen in the normalized high concentration data in FIG. 7b. Second, it also compensated for the attenuation differences between acquisitions at 2.25 MHz in that same figure. Third, it allowed a comparison with single MB simulated data since the measured RM is normalized by the number of MB. Note, however, that this comparison has some limitations. For example, $RM_{SIM}$ did not take LF harmonics into account (HF scattering is computed based on a static MB), and $R_{max}$ and $R_{min}$ in the simulations correspond to an ideal synchronization between LF and HF.

Accordingly, radial modulation is based on the measurement of changes in HF scattering when the MB radius is modulated by a LF. In Example 1, the 2.25 MHz LF produced higher RM than the 1 MHz frequency for MI<0.1. This can be explained by the fact that 2.25 MHz is closer to the mean bubble population resonance frequency (3.5 um). However it was found that RM reached the same peak plateau independently of the LF frequency. This plateau was attained at 0.1<MI<0.15, slightly preceding appearance of LF harmonics (cf FIG. 7c), which was unexpected based on the simulations. One explanation is that the experimental RM reaches a plateau because the synchronization becomes inefficient when non-linear oscillations appear in our experimental setup. Although LF harmonics were not measured in the HF bandwidth, it is very likely that low order harmonics ($2^{nd}$, 3rd) outside of the HF bandwidth could have interfered with the synchronization scheme. A more precise synchronization for 0.1<MI<0.15 could improve RM at either or both frequencies studied, which can be obtained by varying the HF delay independently for each LF pulse. At MI>0.15, further synchronization degradation and the increase in LF harmonics induced an increase of $P_{min}$ thus decreasing RM (see eq.2). As described herein, a different decrease in RM occurred at both frequencies for MI>0.150, with the range of MI being beyond the MI foreseen as ideal for RM imaging because of the presence of LF harmonics.

Also, another potential improvement area is in the tissue cancellation strategy. In FIG. 4. M-mode (Hilbert transformed) amplitude images were subtracted to create the RM image. An RF based subtraction and proper compensation for changes in HF speed of sound due to the LF pressure can further improve the image contrast.

The apparition of harmonics in the experimental data ultimately establishes a maximum MI that is desirably used. LF harmonics, although measured in the high frequency bandwidth, remain at the LF spatial resolution. This can be understood by the time-space relationship used for ultrasound imaging. Indeed, the non-linear oscillations of the MB when excited at high pressure at LF are present for the duration of the LF pulse, which translate directly into a LF resolution, even if measured at high frequency. These harmonics can indicate the presence of MB in the HF field but their spatial position is convolved by the LF pulse length.

Accordingly, Example 1 provided experimental evidence that RM imaging at high frequency can be performed with very efficient tissue signal suppression. In addition, the MI can be relevant in determining the choice of the LF, as the same RM plateau was reached for both frequencies at 0.1<MI<0.15. However below 0.1 MI, a higher RM can be obtained for the same MI near resonance (2.25 MHz). Finally, because this technique involves the subtraction of two successive lines, it can be desirable, at least in some embodiments, that the time interval between two successive frames be kept as small as possible. Since HF ultrasound is typically limited to very shallow penetration depth, RM is well suited for high frequency applications where a very high PRF can be achieved.

Contrast Enhanced Ultrasound Imaging and Coronary Imaging

In the following embodiments, novel intravascular ultrasound (IVUS) imaging methods and apparatuses are provided for achieving molecular imaging and characterization of cardiovascular diseases, such as atherosclerotic plaques. As discussed in more detail herein, the method can include the use of multiple ultrasound frequencies and bubble-based contrast agents, such as those discussed above in connection with RM.

In one embodiment, a low frequency ultrasound burst can be provided to excite a microbubble into oscillation, and a high frequency ultrasound burst is used to image the microbubble while it is going through forced oscillation by the low frequency ultrasound. The method can include using two pairs of such pulses and can utilize the timing of the two ultrasound bursts in each pair. The detail of the pulse waveform can depend on the frequency desired and the kind of contrast agents and its size distribution.

Methods of signal processing that are specific for the pulsing scheme can be used to enhance the microbubble specific signal. Such signal processing can also be configured to cancel or reduce the ultrasound signal from non-bubble targets such as soft tissue. A pair of two dimensional images can be formed during image frames, one that includes the tissue background to provide anatomical information and one that includes enhanced bubble contrast image that may contain information of molecular expression.

In some embodiments, the device can comprise an IVUS system that is capable of dual frequency applications and a specialized imaging catheter. The IVUS system can be configured such that the ultrasound pulse configuration can be changed online according to specific microbubble properties. This can be accomplished, for example, by allowing the center frequency of the low frequency ultrasound to be changed within a range to accommodate different resonance frequencies of the microbubbles, and allow the delay of the imaging pulse relative to the low frequency pulse to be adjusted.

In some embodiments, a delay configuration can be provided such that one of the imaging pulses is temporally located at the positive going zerocrossing of the low frequency pulse while another imaging pulse is temporally located at the negative going zero-cross of the low frequency pulse. Such an arrangement can be desirable, for example, if the low frequency is near the resonance of the microbubbles. In another embodiment, a delay configuration can be provided such that one of the imaging pulses is temporally located at the maximum of the low frequency pulse while the other imaging pulse is temporally located at the minimum of the low frequency pulse.

In some embodiments, the catheter can comprise two concentric ultrasound elements, with the outer element transmitting the low frequency ultrasound and the inner element transmitting and receiving the high frequency signal. In other embodiments, the catheter can comprise two ultrasound transducers next to each other, with one transmitting the low frequency ultrasound and the other transmitting and receiving the high frequency ultrasound. In yet another embodiment, an array of ultrasound elements can be used, with some transmitting the low frequency ultrasound and others transmitting and receiving the high frequency ultrasound. In yet another embodiment, a catheter with a single element can be used to transmit both low and high frequency pulses. In some embodiments, the catheter can be equipped with an injection port to inject bubble-based contrast agents locally.

Visualization of Plaque and Imaging of Vasa Vasorum.

Post-mortem histological data document that vasa vasorum (VV) and intraplaque hemorrhage are critical processes in the progression from asymptomatic into high-risk unstable lesions. VV are vessels that normally provide vascular supply to the blood vessel wall. During atherogenesis, there is abnormal adventitial VV proliferation and intraplaque neovascularization. Increased VV density is strongly associated with plaque rupture and other features of vulnerable plaque, such as a thin fibrous cap, a large necrotic core, and intraplaque hemorrhage. Conversely, it has been found that anti-angiogenic drug rPAI-1(23) treatment and HMG-CoA reductase inhibitors (statins) can reduce adventitial VV density and plaque extent, suggesting that VV could be implicated in plaque progression. These findings suggest that VV and plaque neovascularization are both markers of and etiologic factors in the development of high-risk atherosclerotic plaques.

Contrast enhanced ultrasound (CEUS) imaging using microbubbles (MB) can be used to as a modality for VV imaging in the carotids. Since increased VV density is strongly associated with plaque rupture and other features of vulnerable plaque, such as a thin fibrous cap, a large necrotic core, and intraplaque hemorrhage, levels of VV and plaque neovascularization detected on CEUS carotid imaging correlate with cardiovascular disease and cardiovascular events. However, although non-linear based CEUS carotid imaging can provide an overall measure of proneness to cardiovascular events, it cannot directly visualize high risk features of specific plaques within the coronary arterial tree to predict which plaques are susceptible to rupture. For coronary wall imaging, contrast enhanced IVUS is capable of spatially resolving and detecting VV in the coronary arterial wall in vivo using linear and non-linear approaches. The linear approach relies on the sequential analysis of consecutive video frames before and after the injection of a microbubble bolus. This approach is inherently susceptible to motion artifacts and suffers from poor contrast to tissue ratio.

Non-linear subharmonic and second harmonic approaches can dramatically improve the contrast to tissue ratios in vitro and in atherosclerotic rabbit models, compared to B-mode imaging. However, nonlinear imaging at high frequency can introduce considerable challenges on both the transducer and MB technological fronts. The systems and methods described herein address the shortcomings in conventional technology and provide improved high frequency contrast imaging.

Radial Modulation.

Figure 8:
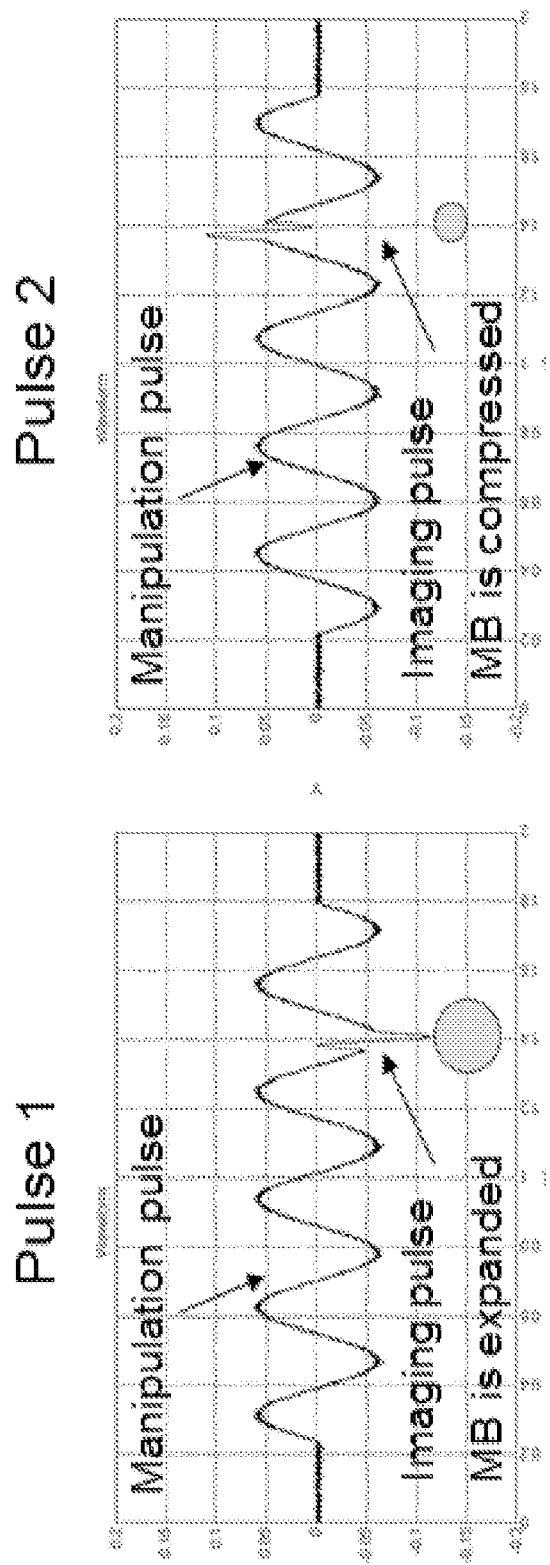
FIG. 8 illustrates the radial modulation principle by showing two pulses having a low frequency (manipulation pulse) pulse and a high frequency (imaging pulse) pulse that are synchronized to successively measure MB scattering while in expanded and compressed states.

As described above, radial modulation (RM) imaging is a dual frequency technique in which a low frequency (LF), also called modulation frequency, is used to manipulate the microbubble size, while high frequency (HF) scattering variations in amplitude and/or phase are monitored. FIG. 8 illustrates the radial modulation principle by showing two pulses having a low frequency (manipulation pulse) pulse and a high frequency (imaging pulse) pulse that are synchronized to successively measure MB scattering while in expanded and compressed states. The pulses can be sent within a very small time interval (~10 μs) to minimize tissue motion between the pulses. Subtracting both high pass filtered scattered signals yields a contrast specific signal. Because tissues do not respond to the LF modulation pulse, they are cancelled out in radial modulation imaging. In some embodiments, herein, the LF is between 1-5 MHz while the HF is between 15 and 50 MHz.

One implementation of RM imaging comprises synchronizing two successive HF pulses such that they reach the microbubble, respectively, in a compressed and an expanded state, as induced by the low amplitude LF pressure wave. By subtracting successive high-pass filtered HF scattered lines, this dual pulse dual frequency approach results in a MB specific RM image, in which tissue scattering is suppressed because it is minimally affected by the LF modulation pulse. RM signal amplitude increases with LF amplitude, but is ultimately limited by the coupling of LF harmonics into the HF bandwidth, severely degrading the resolution.

In this study, a dual frequency IVUS imaging system is provided based on microbubble radial modulation. The system is capable of contrast specific imaging at high resolution (e.g., 25 MHz) and can, in one embodiment, be implemented on a single element rotating catheter. As discussed in more detail below, a LF near MB resonance was found to improve the RM response in a configuration with limited LF pressure delivery, minimize crystal polarization distortion and minimize differences in HF speed of sound with pressure by using an appropriate synchronization phase at LF zero crossing.

As described below, the effects of microbubble size distribution and HF/LF synchronization on the RM signal amplitude and polarity were analyzed using simulations, and the RM IVUS imaging system was evaluated in a wall-less tissue mimicking phantom perfused with microbubbles. In addition, the effects of the HF/LF synchronization on RM signal amplitude and polarity were quantified and the system was characterized in terms of contrast to tissue (CTR) and contrast to tissue improvement (CTRI) ratios as a function of depth, LF pressure and MB concentration. The cancellation of flowing blood were also assessed and the ability of RM imaging for the detection of MB circulating in a 200 µm cellulose micro-tubing embedded in tissue mimicking material was analyzed.

Example 2

As indicated above, the MB RM response of a single MB can be predicted using thin-shelled microbubble oscillation theory. The simulation package "Bubblesim" was used in this example to estimate the maximal and minimal radii of MB ranging from 1 to 10 µm, when submitted to a 5 cycle 3 MHz LF pulse. Shell viscosity was chosen as 0.8 Pa·s, shear modulus as 50 MPa and shell thickness as 4 nm, corresponding to thin shelled lipid encapsulated MB. The Raleigh-Plesset liquid model with radiation damping coupled to an isothermal gas phase was solved using the stiff variable order solver. At 25 MHz, (ka~0.15, k is the wave number and a, the scatterer radius) backscattered power is proportional to the scatterer geometrical cross section. Hence, the RM contrast for a single MB can be estimated as:

$$RM_{OPT} = \frac{R\text{max}^2 - R\text{min}^2}{R^2}, \quad \text{(eq. 3)}$$

where $R_{max}$ and $R_{min}$ are respectively the simulated bubble radius at maximal and minimal expansion and R is the MB equilibrium radius. $RM_{OPT}$ is, by definition, the optimally synchronized RM response, and is easily found in simulations by analyzing R(t).

In practice, the HF pulse has a finite length and a fixed HF timing can be chosen with respect to the LF cycle. Synchronizing the HF pulse to reach all MBs at maximal and minimal expansion is not possible, especially for a polydispersed MB suspension, where MB may oscillate with different phases in response to the LF pulse. The effect of MB size polydispersity on the RM signal amplitude and polarity was therefore investigated by simulation using a 5 cycle 3 MHz LF pulse and a 2.5 cycle 25 MHz HF pulse positioned at different HF/LF synchronization phases. The HF pulse was positioned between the third and fourth cycle of the LF pulse 1. The synchronization phase referred to in the rest of the paper is relative to the third positive pressure peak in LF pulse 1, i.e. "0 synchronization phase" refers to the HF pulse positioned at the third positive peak of LF pulse 1, and 2π synchronization phase corresponds to the fourth positive peak of LF pulse 1. For each HF/LF synchronization phase, the mean RM signal during each HF pulse was calculated as:

$$RM_{SIM} = \frac{\overline{R_1}^2 - \overline{R_2}^2}{R^2}, \quad \text{(eq. 4)}$$

where $\overline{R_1}$ and $\overline{R_2}$ are respectively the mean MB radii during HF pulses, R is the equilibrium radius. These simulations were performed for MB sizes ranging from 1 to 10 µm and synchronization phases varying from 0 to 2π.

Although several exemplary phase arrangements are described herein, it should be understood that alternative phase arrangements are contemplated and, in some cases, desirable, depending on the system parameters, including, for example, vessel red cell content, distance of targets of interest from the transducer (depth), choice of specific HF, and MB size. In some embodiments, the phase arrangement can be varied during imaging to fine-tune or otherwise improve the desired results from the imaging process.

Figure 9:
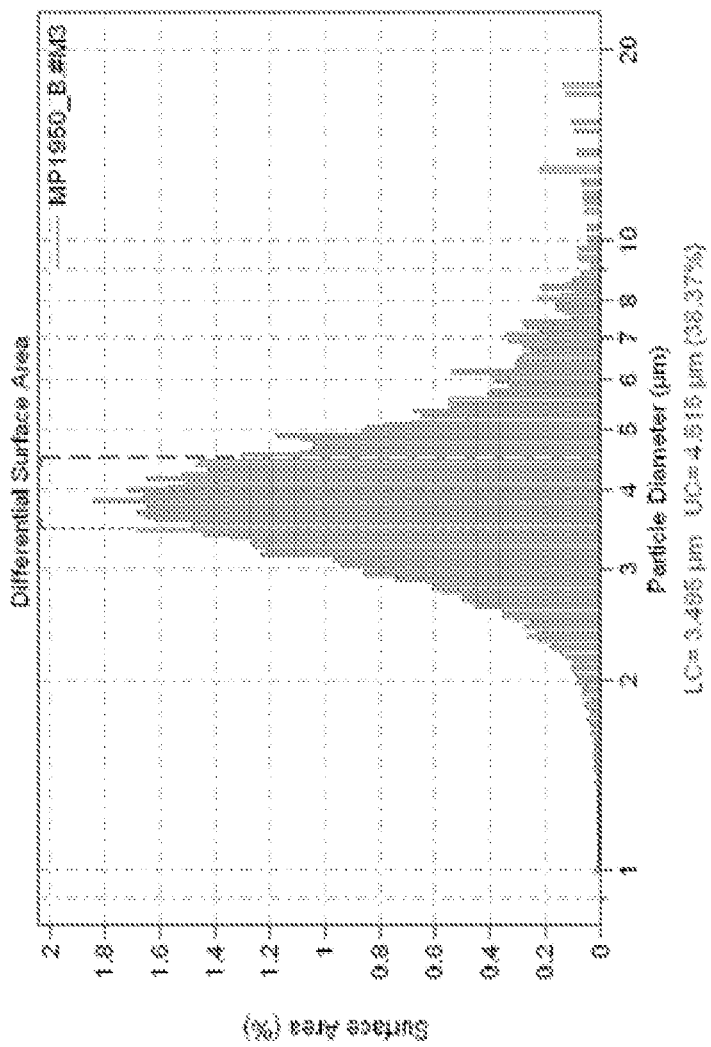
FIG. 9 illustrates properties of an embodiment of lipid encapsulated MBs.

As shown in FIG. 9, lipid-encapsulated perfluorocarbon MB (4.1±1.3 µm, surface weighted) were measured (Beckham Coulter Multisizer3, Brea, Calif.), and circulated at a flow rate of 9 mL/min in a 6 mm diameter wall-less cylindrical agar based phantom containing 2% sigma-cell (20 µm particles, Sigma-Aldrich, Saint Louis, Mo.) to mimic tissue scattering. 38% of the MBs were in the 3.5-4.5 size range.

A single element rotating catheter (Sonicath Ultra 3.2, Boston Scientific, Fremont, Calif.) was placed against the "wall" of the phantom to allow comparison of contrast and tissue signals as a function of depth. In a separate set of experiments, a similar 4 mm wall-less phantom also containing 2% sigma-cell was built and 200 µm cellulose micro-dialysis hollow fibers (Spectra/Por, Spectrum Laboratories, Rancho Dominguez, Calif.) were placed in the wall and perfused with microbubbles. Citrated porcine blood and MB were also circulated at a mean velocity of 20 cm/s and imaged at the rotation speed of 30 Hz to assess the effect of flow on tissue cancellation.

Figure 10:
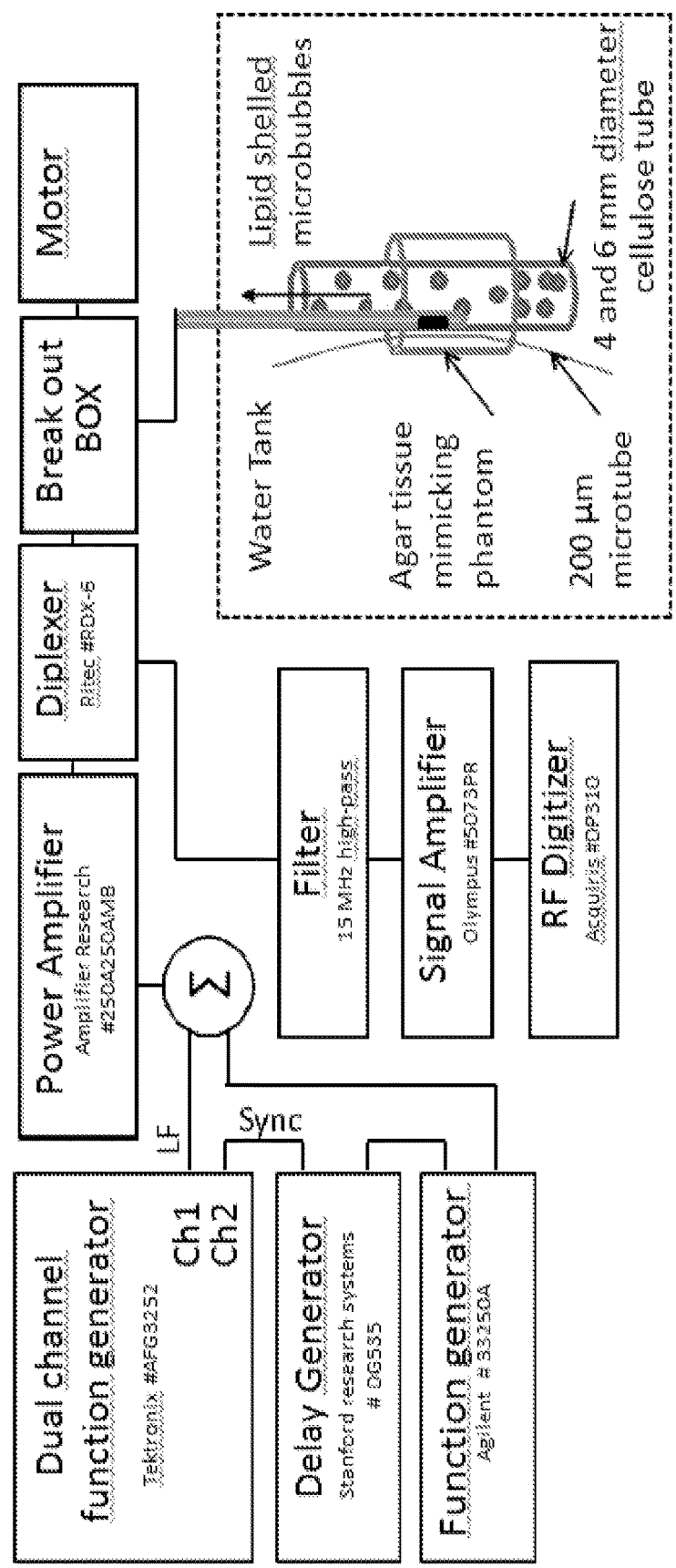
FIG. 10 illustrates an exemplary system for providing contrast assisted ultrasound imaging.

FIG. 10 illustrates a schematic view of the system. The RM system comprised a 20 MHz single element rotating catheter (Sonicath Ultra 3.2, Boston Scientific, Fremont, Calif.), connected through a breakout box (provided by Boston Scientific) to custom pulsing and receiving electronics and to a motor for rotation at 2.6 Hz. Two 5-cycle 3 MHz LF pulses with inverted phases were generated on channel 1 of a dual channel function generator (Tektronix AFG3252, Beaverton, Oreg.), separated by a 14 µs interval. Channel 2 of the same apparatus was used to generate two trigger signals used to gate the power amplifier (250A250AMB, Amplifier Research, Souderton, Pa.) (to reduce noise in reception) and to trigger a second function generator (33250A, Agilent, Santa Clara, Calif.) which generated the 2.5 cycle 25 MHz HF pulses. The trigger signals were relayed by a delay generator (Model DG535, Stanford research systems, Sunnyvale, Calif.) to vary the HF/LF synchronization phase. The HF and LF pulse were then summed using a power splitter/combiner (ZSC-2-1W+, Mini-circuits, Brooklyn, N.Y.) and amplified by 55 dB by the power amplifier. Two diplexers (model RDX-6, Ritec, Warwick, R.I.) were inserted in series to further reduce the noise. The excitation pressure pulses were measured by a 200 µm aperture calibrated hydrophone (HGL-0200, Onda Corp, Sunnyvale, Calif.). Of course, various other arrangements are contemplated. For example, one or more elements of the above-described setup can be integrated into the system itself or otherwise utilized as an external plug-in.

Figure 11:
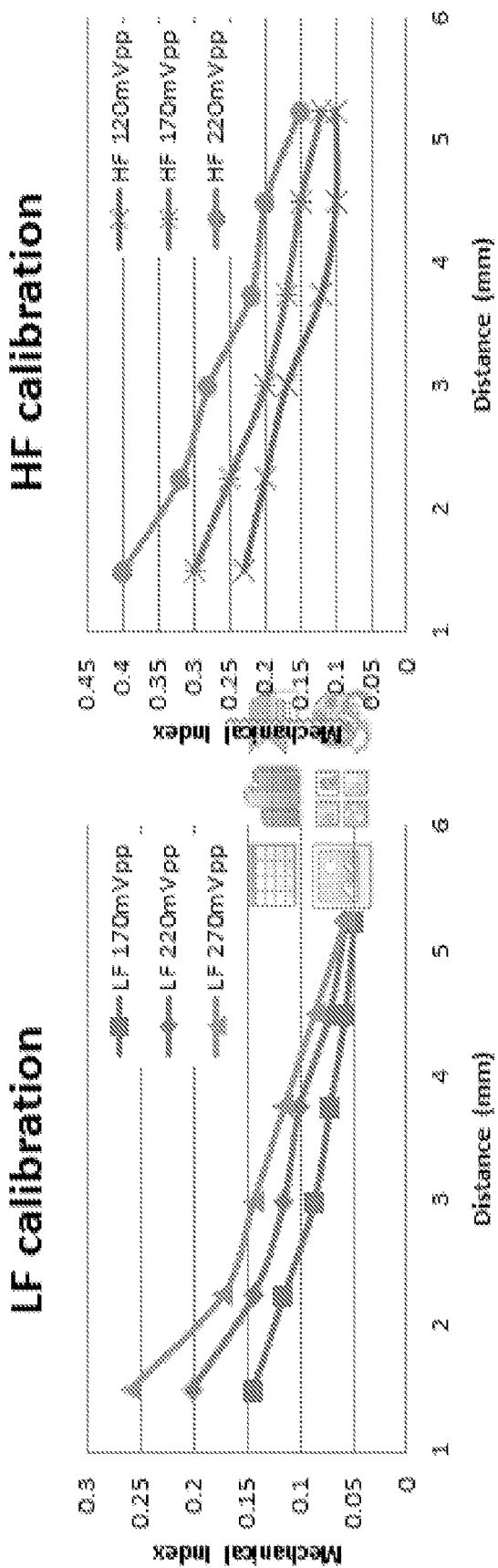
FIG. 11 illustrates LF and HF pressures displayed as a function of distance.

LF and HF pressures are displayed as a function of distance in FIG. 11, which illustrates the mechanical indices of the low frequency (LF) 3 MHz manipulation pulse and high frequency (HF) imaging pulse as a function of depth for three excitation voltages (before amplification). LF and HF MI decrease as a function of depth.

Figure 12:
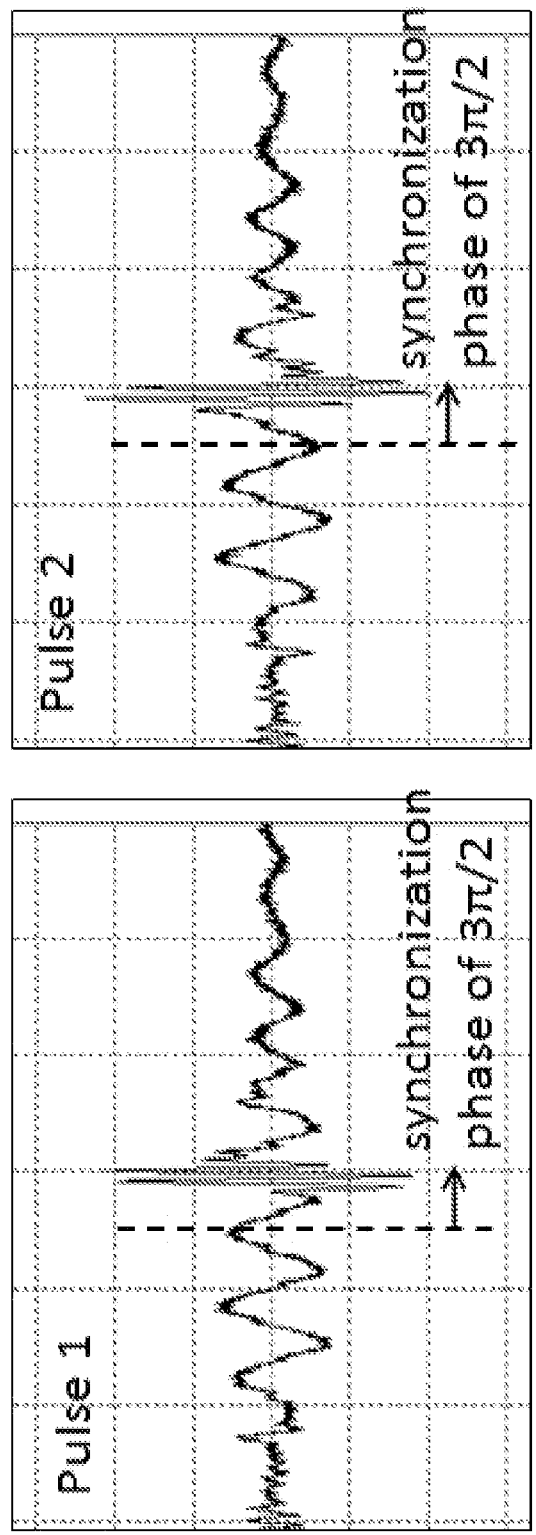
FIG. 12 illustrates an exemplary pair of dual frequency RM pulses.

A typical pair of dual frequency RM pulses is also shown in FIG. 12. In particular, FIG. 12 illustrates hydrophone measurements showing a pair of pulses used for RM imaging, measured at 2 mm from catheter center. The HF pulse is centered at the $3^{rd}$ negative to positive zero crossing of LF pulse 1 and $3^{rd}$ positive to negative crossing of LF pulse 2. LF pulses have an inverted phase. HF pulses have the same phase. This corresponds to a HF/LF synchronisation phase of 3π/2, centered around the negative to positive zero-crossing of LF pulse 1.

The HF/LF synchronization was varied using the delay generator. Pairs of pulses were sent at a repetition rate of 416 Hz for a line density of 160 lines/rotation. On reception, the radio frequency signal was amplified by 35 dB (5073PR, Olympus, Waltham, Mass.) and high-pass filtered (15 MHz). RF signals were digitized at a sampling frequency of 400 MHz (Acquiris DP310, Agilent Technologies, Santa Clara, Calif.) and stored for offline processing. RF data were numerically band-pass filtered ($4^{th}$ order Butterworth, 17-28 MHz) and Hilbert transformed before line to line subtraction to generate RM images. Finally, RM images were median filtered using a 15×3 pixels window before display and analysis.

The effect of varying the HF position within one LF cycle, MB concentration and LF amplitude was analyzed as a function of depth. Regions of interest (ROI) were manually selected at increasing depths in the lumen and in the tissue in the acquired images. They were used to compute the experimental normalized RM ($RM_{EXP}$), RM signal from the MB ($RM_{MB}$), RM signal from tissue ($RM_T$), RM contrast to tissue ratio ($CTR_{RM}$), B-mode CTR ($CTR_{B-mode}$), and CTR improvement (CTRI), respectively calculated using:

$$RM_{EXP} = 2\frac{\overline{P_1} - \overline{P_2}}{\overline{P_1} + \overline{P_2}} \quad \text{(eq. 5)}$$

$$RM_{ROI} = 20 * \log_{10}[Hilbert(ROI_{Image1}) - Hilbert(ROI_{Image2})] \quad \text{(eq. 6)}$$

$$CTR_{RM} = RM_{MB} - RM_T \quad \text{(eq. 7)}$$

$$CTR_{B-mode} = Bmode_{MB} - Bmode_T \quad \text{(eq. 8)}$$

$$CTRI = CTR_{RM} - CTR_{B-mode}, \quad \text{(eq. 9)}$$

where $\overline{P_1}$ and $\overline{P_2}$ are respectively the mean backscattered power in the −6 dB HF bandwidth for pulse 1 and 2, $ROI_{image1}$ and $ROI_{image2}$ are the same region of interest in images 1 and 2, and Hilbert stands for the Hilbert transform. $RM_{EXP}$ is normalized in (eq.5) for coherence with simulation data. The CTRI is a parameter that measures the improvement in MB signal independently of MB concentration, and allows comparing different MB imaging strategies.

It should be understood that the methods of data processing for image formation described herein can vary, if desirable. For example, in some embodiments, direct RF subtraction (or other methods) can be used during data processing for image formation.

The presence of LF harmonics was also measured by passively recording the HF scattering without sending HF pulses. Experiments were repeated three times (one time for phase experiment) and results are shown as mean±standard deviation.

Example 2

Results

Figure 13:
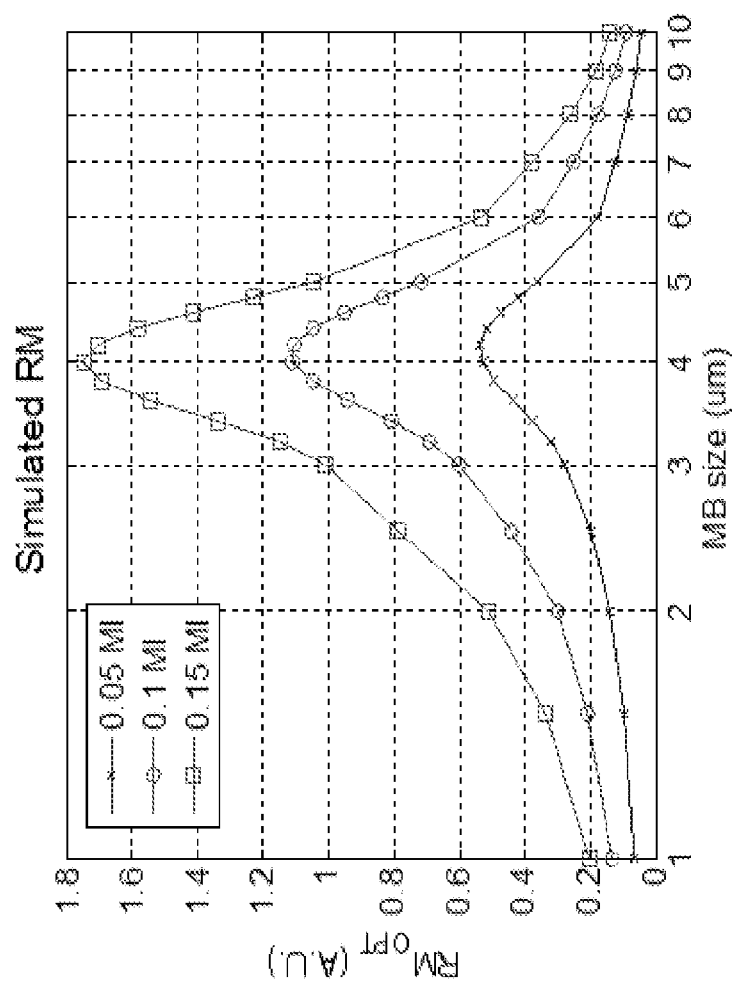
FIG. 13 illustrates $RM_{OPT}$, an optimal RM response, plotted as a function of MB size and LF mechanical index (MI).

The RM response of MBs with sizes varying from 1 to 10 µm was first investigated by simulation for an LF frequency of 3 MHz. As shown in FIG. 13, $RM_{OPT}$, the optimal RM response, is plotted as a function of MB size and LF mechanical index (MI). FIG. 13 shows that the oscillations of MBs of sizes ranging from 1 to 10 µm were simulated using a 3 MHz 5 cycle LF pulse. The maximal and minimal MB expansion were determined using the R(t) response and used to calculate the optimal RM response using eq.3. $RM_{opt}$ was found to increase with the MI and was maximal for MB of 4 µm.

$RM_{OPT}$ peaked for MB sizes around 4 µm, corresponding to the theoretical lipid MB resonant size and decreased for MB of other sizes. RM increased with LF amplitude, as previously reported by us and others. However, in practice, MB sizes are polydispersely distributed and a fixed HF timing can be chosen within the LF cycle for imaging. Therefore, the effect of varying HF synchronization phase was also investigated by simulation as a function of MB size, as illustrated in FIG. 14.

Figure 14:
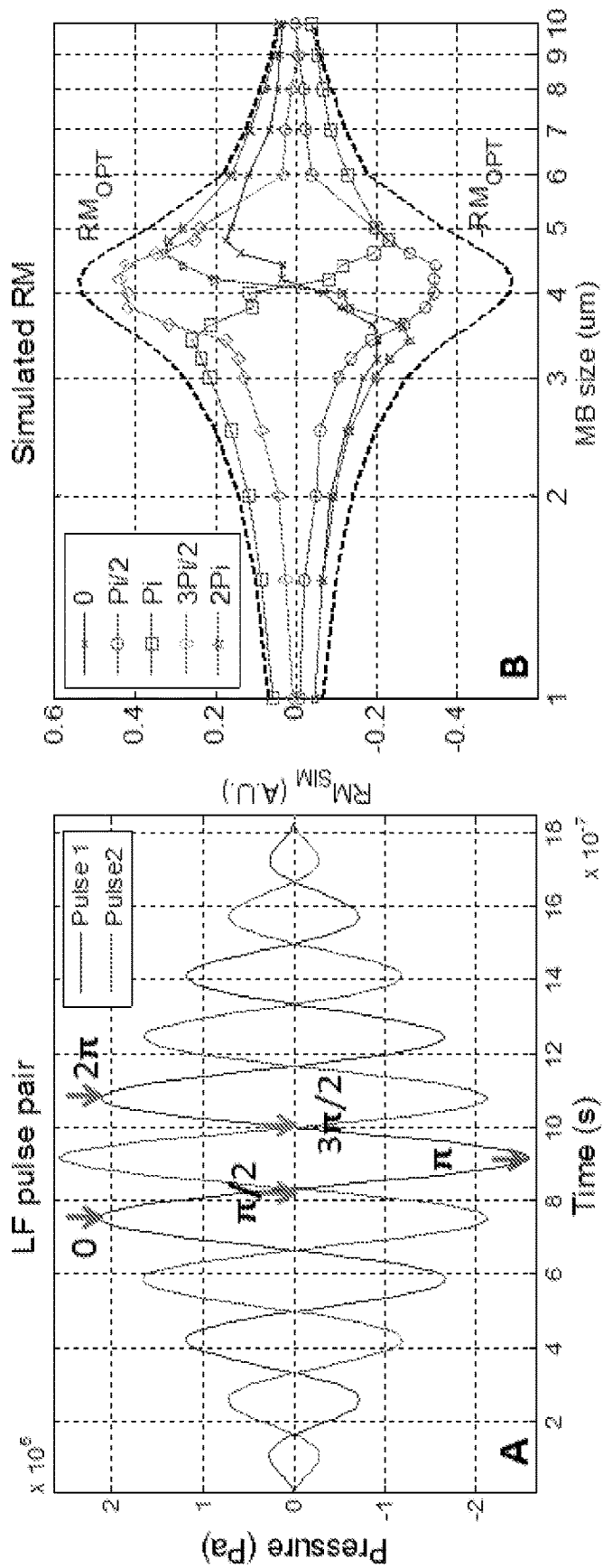
FIG. 14 illustrates the effect of varying HF synchronization phase by simulation as a function of MB size.

As shown in FIG. 14, the synchronization phase was varied over one LF cycle (arrows in panel A) and the corresponding RM response as a function of the MB size was calculated using eq.4 (panel B). $RM_{OPT}$, determined in FIG. 13, is also reported in panel B for comparison. With a fixed synchronization phase and a 2.5 cycle HF pulse duration, the RM response was MB size dependent. At a phase of π, MBs smaller than 4 µm had a positive RM response whereas MBs larger 4 µm had a negative RM response. At 3π/2, RM was maximal and strictly positive for all MB sizes. At 2π, MBs smaller than 4 um had a negative RM response whereas MBs larger 4 µm had a positive RM response.

When HF is positioned near LF pulse 1 peak, (i.e., 0 HF/LF synchronization phase), the RM signal is positive for larger MB and negative for smaller MB. This behavior can be explained by first order damped oscillator theory: MB smaller than resonance oscillate in phase with the pressure pulse (MB is small when pressure in high), whereas MB larger than resonance oscillate with opposite phase with respect to pressure (MB is big when pressure is high). At this synchronization phase, resonant MB are near equilibrium size and do not contribute to RM. The net RM signal with this synchronization phase can be positive or negative, depending on the MB population distribution (a larger number of bigger MB will result in net positive RM signal). When HF is positioned at LF pressure zero crossing (i.e. π/2 and 3π/2 synchronization phases), RM reached maximal amplitude and RM signal across all MB sizes were respectively either negative or positive, which can be explained by the fact that at this timing, large and small MB are near equilibrium size and the RM signal is mainly the result of resonant MB oscillations. In addition, RM amplitude was maximal near MB resonance, which corresponds to the HF synchronized at π/2 and 3π/2 and was strictly positive or negative for all MB sizes. At this synchronization phase, the simulations indicated that only a fraction of the MB population, with sizes between 3.5 and 4.5 µm (−3 dB threshold), was contributing to the RM signal at 3 MHz.

In Vitro Experiment: Effect of Phase, MB Size and Single Element Catheter Implementation.

Figure 15:
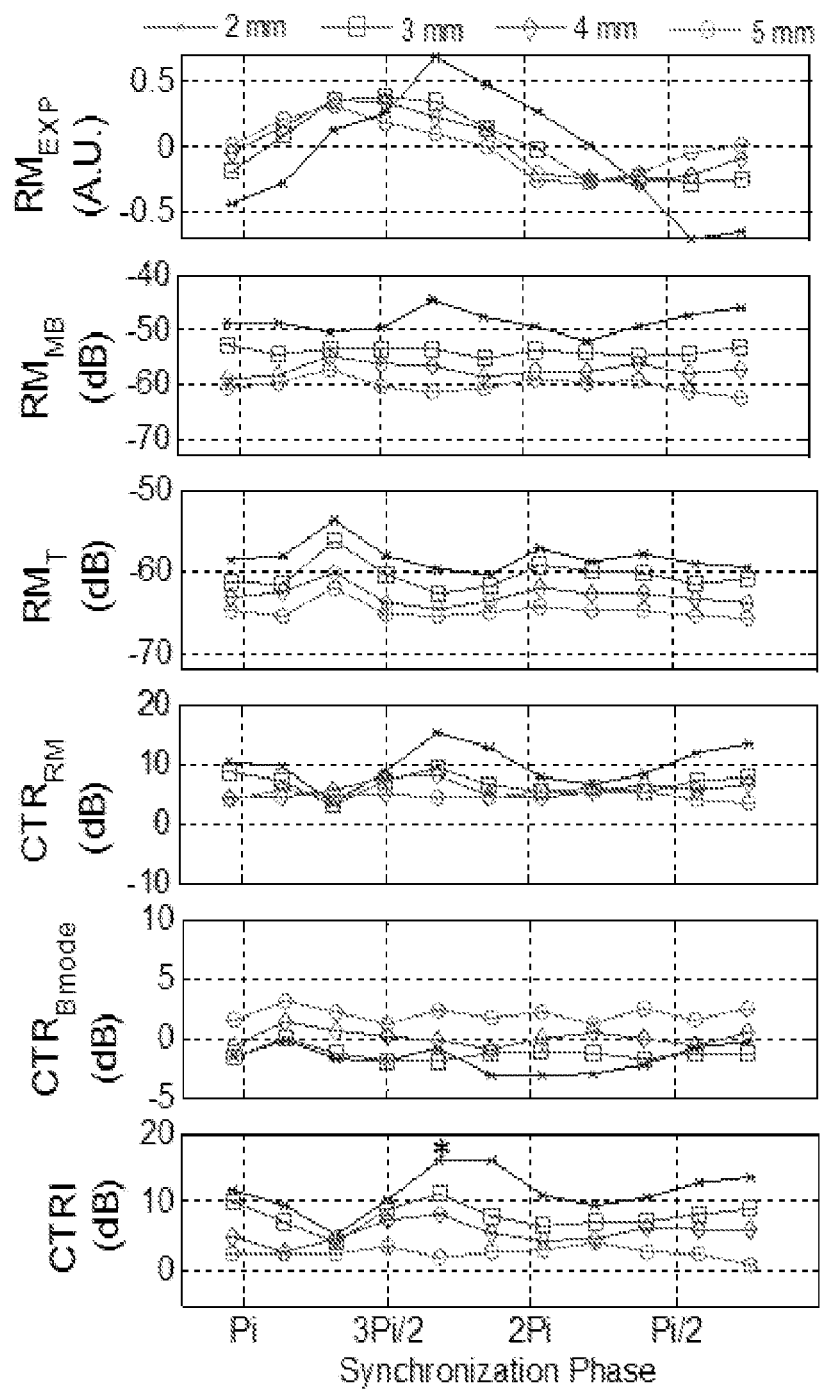
FIG. 15 illustrates experimental RM quantified using indicated parameters as a function of HF/LF synchronization phase for different depths, with a fixed LF amplitude of 220 mVpp and MB concentration of $6.4 \times 10^5$ MB/mL.

FIG. 15 illustrates experimental RM quantified using indicated parameters as a function of HF/LF synchronization phase for different depths, with a fixed LF amplitude of 220 mVpp and MB concentration of 6.4×10⁵ MB/mL. All parameters were calculated in ROI of 1 mm centered at 2, 3, 4, and 5 mm from the catheter center using equations 3 to 7. CTR and CTRI were maximal for a phase slightly larger than 3π/2 ($Phase_{OPT}$, marked by an asterisk) which was chosen for the rest of the study.

The first panel of FIG. 15 shows that for 3, 4 and 5 mm data, $RM_{exp}$ was maximal and positive at synchronization phase of 3π/2, crossed 0 at phases of 0 and π and was negative at a phase of π/2. This is coherent with resonant MB behavior, as described in the simulation in FIG. 13.

However, for 2 mm data, RM was shifted to the right, peaked positively between $3\pi/2$ and 0 and negatively between $\pi/2$ and $\pi$. This suggests, when looking at the results described herein, that bigger MBs in the population were dominating the RM response close to the catheter, where pressure was higher. The reason why resonant MB were not dominating the RM signal close to the catheter could be that they are driven beyond linear oscillations, which conflicted with the synchronization scheme. At that synchronization phase (Phase$_{OPT}$, indicated by an asterisk in FIG. 15), RM$_{MB}$ and RM$_T$ respectively reached maximal and minimal values. CTR$_{RM}$ and CTRI correspondingly peaked at 15.2 and 16.0 dB for the 2 mm data, respectively down to 4.1 and 1.9 dB at 5 mm. At that synchronization phase, RM$_T$ was minimal and below −60 dB at all depths. CTR$_{BM}$ was independent of the phase and increased with distance, which is indicative of LF radiation force pushing MB away from the catheter. This was also observed on multi-frame acquisitions (not shown).

LF Amplitude.

Figure 16A:
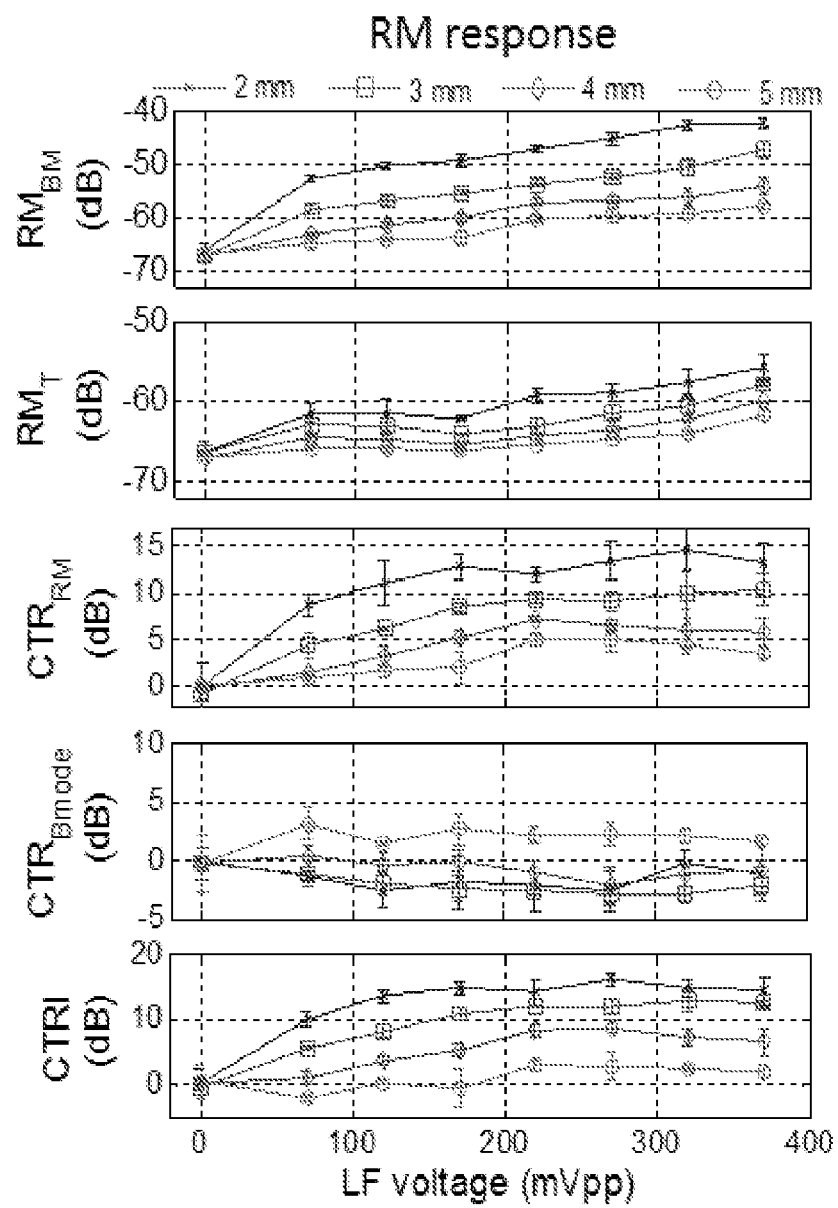
FIGS. 16A and 16B illustrate experimental RM quantified using indicated parameters as a function of LF amplitude for different depths, with fixed phase of $37\pi/2$ and MB concentration of $6.4\times10^5$ MB/mL.
Figure 16B:
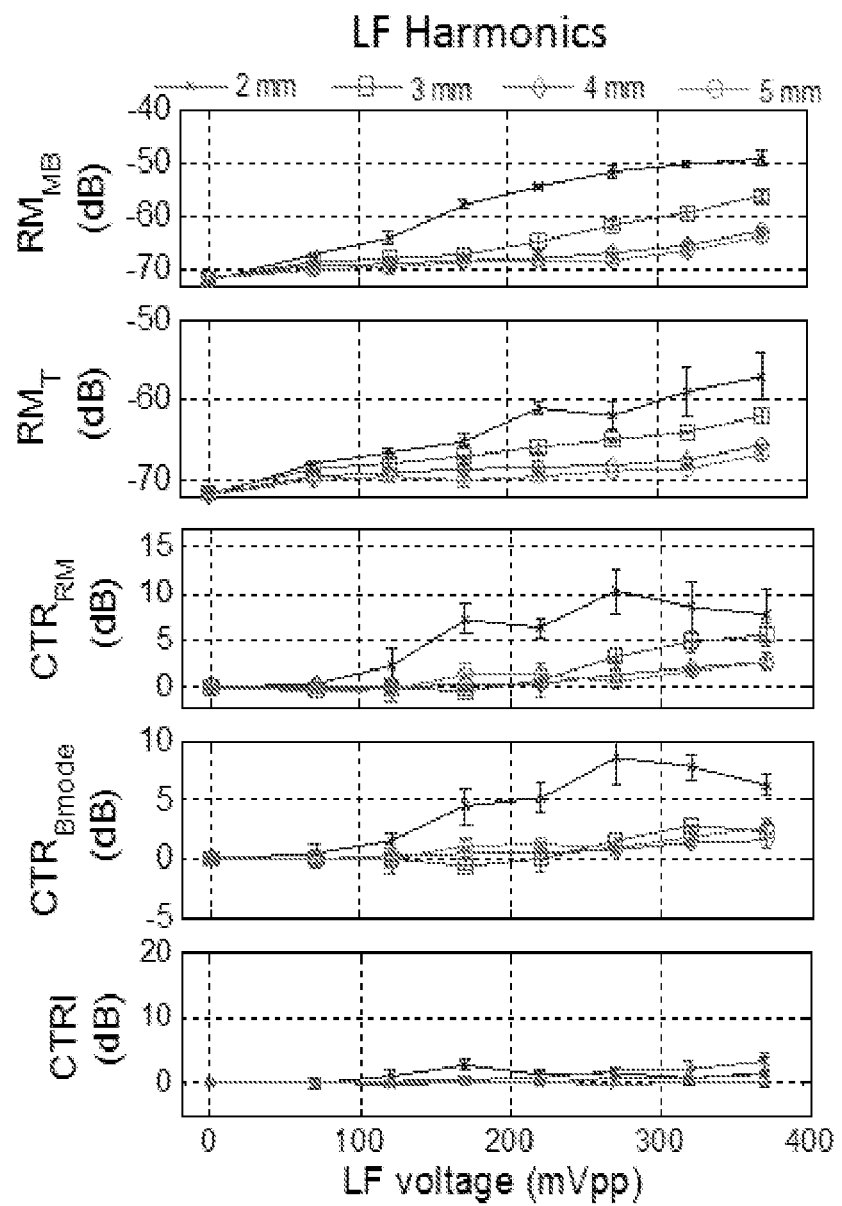

The HF synchronization and MB concentration were fixed at Phase$_{OPT}$ and $6.4\times10^5$ MB/mL and the LF amplitude was varied. FIGS. 16A and 16B illustrate experimental RM quantified using indicated parameters as a function of LF amplitude for different depths, with fixed phase of $3\pi/2$ and MB concentration of $6.4\times10^5$ MB/mL. All parameters were calculated in ROI of 1 mm centered at 2, 3, 4, and 5 mm from the catheter center using equations 3 to 7. In the left panel, RM pulsing was used; in the right panel, HF pulses were turned off to quantify the contribution of LF Harmonics to the parameters. Measurements were repeated 3 times.

FIG. 16A indicates that RM$_{MB}$ and RM$_T$ increased with LF amplitude, but CTR$_{RM}$ and CTRI plateaued at 220 mVpp. At this excitation amplitude, corresponding to 0.17 MI at 2 mm, CTR$_{RM}$ decreased from 12.0±0.9 dB at 2 mm to 5.1±0.6 dB at 5 mm. This corresponded to a CTRI of 14.2±1.8 dB at 2 mm down to 3.0±0.7 at 5 mm. In FIG. 16B, HF pulses are turned off and the parameters reflect the contribution of LF harmonics infiltrating the RM signal. LF harmonics are caused by MB non-linear oscillations that propagate into the HF frequency band and should be avoided because they deteriorate the resolution (harmonics are present for the duration of the MB LF oscillations, i.e. 5 cycles). LF harmonics appeared mostly near the catheter (2 mm depth) and accounted for up to 6.4±1.1 dB of contrast signal at 2 mm.

Effect of Varying MB Concentration.

Figure 17:
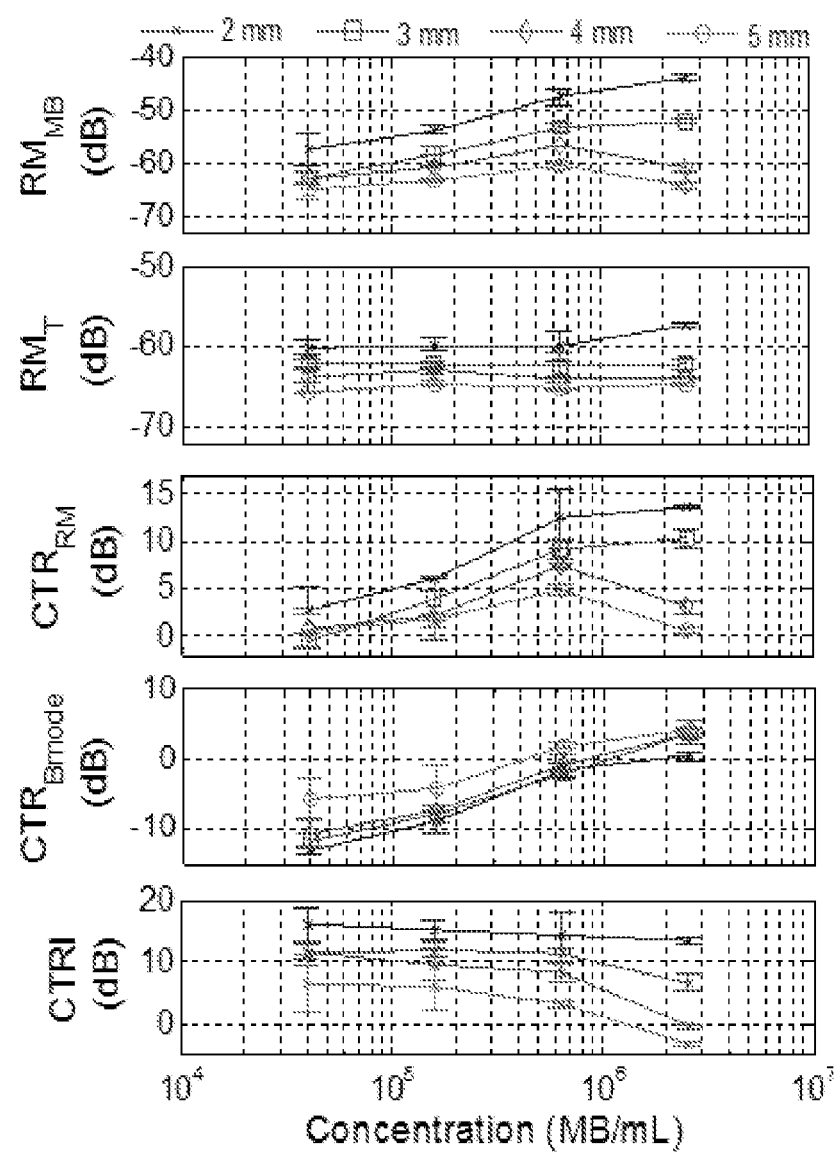
FIG. 17 illustrates experimental RM quantified using indicated parameters as a function of MB concentration.

Finally, the HF synchronization and LF voltage were fixed at Phase$_{OPT}$ and 220 mVpp and the MB concentration was varied. FIG. 17 illustrates experimental RM quantified using indicated parameters as a function of MB concentration, with a fixed LF amplitude and phase of 220 mVpp and Phase$_{OPT}$. All parameters were calculated in ROI of 1 mm centered at 2, 3, 4, and 5 mm from the catheter center using equations. Measurements were repeated 3 times. RM$_{MB}$, CTR$_{RM}$ and CTR$_{B\text{-}mode}$ increased with concentration at 2 and 3 mm but CTRI did not. At 4 and 5 mm depths RM$_{MB}$, CTR$_{RM}$ and CTRI also increased with concentration but decreased at the highest concentration of $2.4\times10^6$ MB/mL. This was due to MB attenuation.

B-Mode and RM Mode Images.

Figure 18:
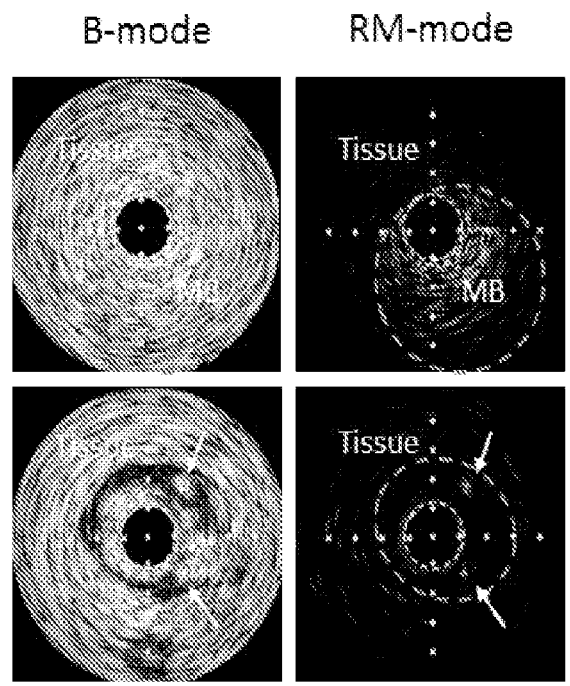
FIG. 18 illustrates examples of B-mode and RM images (synchronization phase of $Phase_{OPT}$, LF amplitude of 220 mVpp and MB concentration of $6.4\times10^5$ MB/mL).

Typical examples of B-mode and RM images (synchronization phase of Phase$_{OPT}$, LF amplitude of 220 mVpp and MB concentration of $6.4\times10^5$ MB/mL) are shown in FIG. 18. In the top panel of FIG. 18, IVUS B-mode and RM images of MBs are illustrated infused in a 6 mm diameter wall-less 2% (w/w) agar tissue mimicking phantom containing scatterers (20 μm Sigmacell, Sigma-Aldrich) at a mean flow rate of 9 mL/min and imaged at 2.6 Hz rotation speed, corresponding to the experimental conditions in FIGS. 16 to 18. The catheter is positioned against the "vessel" wall. In B-mode, tissue and MB are difficult to distinguish from each other. In RM-mode, MB signal remains while tissue scattering is strongly suppressed. RM signal from MB is modulated by depth and is visible up to 4 mm in depth.

In the bottom panel of FIG. 18, MBs are infused in two 200 μm tube (indicated by arrows at 1 and 5 o'clock in the B mode image), placed in heterogeneous tissue surrounding the flow phantom, in parallel with the longitudinal axis. These images were acquired near the edge of the tube where some phantom material had accumulated. The vessel lumen (dark in the B-mode image), partly filled with loose wall material, is infused with water. The heterogeneous tissue material appears dark while the MBs in the micro tubes are visible in the RM image (arrow). MB concentration is $6.4\times10^5$ MB/mL. Wall-less vessel boundary is drawn in orange. Yellow dots are separated by 1 mm. The dark circle in the center is the space occupied by the transducer. Dynamic ranges are respectively 40 dB and 30 dB for the B-mode and RM-mode images.

Blood Cancellation Image.

One drawback of multi-pulse imaging techniques is sensibility to motion artifacts, which can be caused in this geometry by movement artifacts and catheter rotation. Our system characterization was performed at a frame rate of 2.6 Hz and low MB velocities. These parameters were chosen to limit the total energy delivered to the catheter at the higher voltage settings and the amount of MB used. Once an optimal set of parameters was determined, the effect of these limitations was analyzed by acquiring images at native IVUS 30 Hz rotation speed, while circulating blood and MBs at 20 cm/s, a velocity found in coronary circulation. RM$_T$ decreased from −57.6±0.6 dB at 2 mm down to −63.5±0.3 dB at 5 mm, slightly higher than the values found at slow rotation speed (respectively −59.3±0.9 dB at 2 mm and −65.5±0.1 dB at 5 mm). RM signal from blood was very low, −64.1±0.6 dB at 2 mm and −65.7±0.8 dB at 3 mm respectively. CTR$_{RM}$ were 7.4±0.1 dB at 2 mm and 7.3±0.1 dB at 3 mm and CTRI of 5.6±0.1 dB and 7.3±0.1 dB respectively. Note that this particular dataset was obtained with a MB suspension with suboptimal size (2.5±1.1 μm). Nevertheless, these data show that blood and tissue signal were suppressed while MB signal were enhanced in the RM images.

The results indicate that the radial modulation approaches described herein with a 25/3 MHz combination can produce MB specific imaging, with significant tissue and flowing blood signal cancellation. By driving MB near resonance frequency using a synchronization phase of Phase$_{OPT}$, the contrast to tissue signal improvement over B-mode was 14.2±1.8 dB at 2 mm down to 3.0±0.7 at 5 mm at an excitation amplitude of 220 mVpp, corresponding to LF MI of 0.17 at 2 mm and 0.06 at 5 mm. LF harmonic infiltration was found near the catheter, and contributed for 6.4±1.1 dB of the RM signal at a depth of 2 mm (e.g., FIG. 16). These harmonics can result in a degradation of the resolution in the vicinity of the catheter, but this was not observed in the micro tube data (FIG. 18, bottom panel), which could be attributed to increased damping of MB oscillation in the micro tube. RM from tissue and LF harmonics otherwise remained below −60 dB at this excitation amplitude. MB can be detected up to depths of 4 mm with CTR$_{RM}$ above −60 dB, as shown in FIGS. 16 and 18. Such depths are sufficient for coronary wall imaging. The system could also resolve 200 μm tube perfused with MB, placed at 1.5 and 2 mm distance from the center of the catheter, which is helpful for VV imaging.

Compared to other IVUS imaging approaches for VV imaging, this method provides several advantages, including the ability to be used with commercially available catheters, which can help fast track clinical translation. Also, because of a short inter-pulse delay (14 μs), the method should be less sensitive to motion related artifact compared to the linear approach, which is based on frame to frame video-sequence analyses and provide much better contrast to tissue compared with B-mode. Moreover, the performances described herein can be further optimized using monodispersed MBs, as discussed in more detail below.

One challenge in implementing RM imaging on a single element pertains to the transmission of the LF pulse. A 20 MHz crystal can produce significant pressure levels at 3 MHz, for a HF/LF ratio near 10, a recommended rule of thumb for radial modulation imaging, which allows to snapshot the MB oscillation with the HF pulse during the LF driven MB oscillation. Due to the geometry of the catheter element, the pressure pattern of the LF pulse decayed rapidly with distance. The MB near resonance can partly compensate for this decay by producing more RM signal than non resonant MB for the same level of LF pressure. Accordingly, in some embodiments, the geometry can impose a compromise between near field harmonics generation (2 mm) and far-field sensibility (4 and 5 mm data).

Another limitation in using a single element to transmit both LF and HF pulses is that the HF point spread function (PSF) was not perfectly identical between the two pulses and varied with the HF synchronization (data not shown). This was likely caused by polarization of the crystal by the LF voltage. The consequence of this bias can be seen in FIG. 15, in which $RM_T$ (no MBs) varied with the HF synchronization. It was not surprising to find that the highest $RM_T$ signals were found near LF1 valley ($\pi$) and peak ($2\pi$), when the crystal was strongly polarized by the LF voltage. This bias was minimal when the HF was located at the zero crossing of the pressure wave to reduce the polarization, logically corresponding to the minimal $RM_T$ signal in FIG. 8. Taking the Hilbert transform of the HF signal before image subtraction can at least partially compensate for the slight differences in HF pulses PSF, providing better performance (higher CTRI) than pure RF subtraction (data nor shown). It is understood that taking Hilbert transformed data decreases RM sensitivity to RM phase modulation, and that identical HF PSF could enhance the overall performance. Accordingly, in some embodiments, the use of a dual element transducer geometry can be beneficial.

It is known that the speed of sound in tissue is pressure dependent. Variations of the HF pulse propagation speed have been reported to increase the tissue noise in RM imaging and can be compensated for. This effect is likely minimal in the disclosed embodiments because: (1) the penetration depth is very short in IVUS (0.16% change in speed of sound in water for a 350 kPa of pressure, equivalent to 4 μm at 5 mm), several order of magnitude smaller than the axial resolution; (2) we have placed the HF at zero crossing of the LF pressure pulse which reduces the pressure experienced by the HF pulse; and (3) Hilbert transform before image subtraction reduces sensitivity to phase variations between the pair of HF pulses.

Implementations of conventional RM imaging generally use lower than MB resonance LF frequency. In that configuration, MB are smaller than resonant size and oscillate in phase with the LF. In our implementation, tuning the LF to MB resonance had the benefits of: (1) requiring less LF pressure to induce MB oscillation; (2) positioning the HF pulses at LF zero crossing for reduced polarization and variation of the speed of sound with pressure; and (3) generating RM signal with a single polarity (only positive RM) across MB sizes. RM signal therefore added up constructively using this timing within the ultrasound field.

Figure 19:
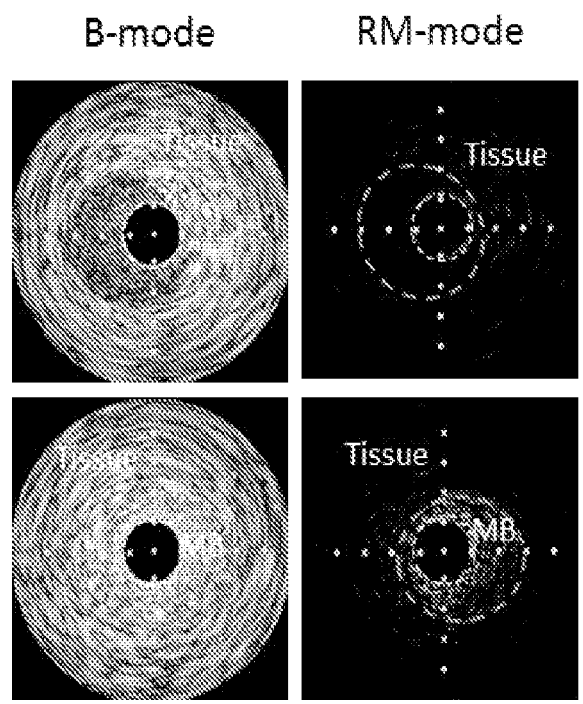
FIG. 19 illustrates IVUS B-mode and RM images of citrated blood (top) and MB (bottom) circulated at a mean velocity of 20 cm/s (150 mL/min) in a 4 mm wall-less 2% (w/w) agar tissue mimicking phantom containing scatterers (20 µm Sigmacell, Sigma-Aldrich), with the catheter rotating at 30 Hz.
Figure 20:
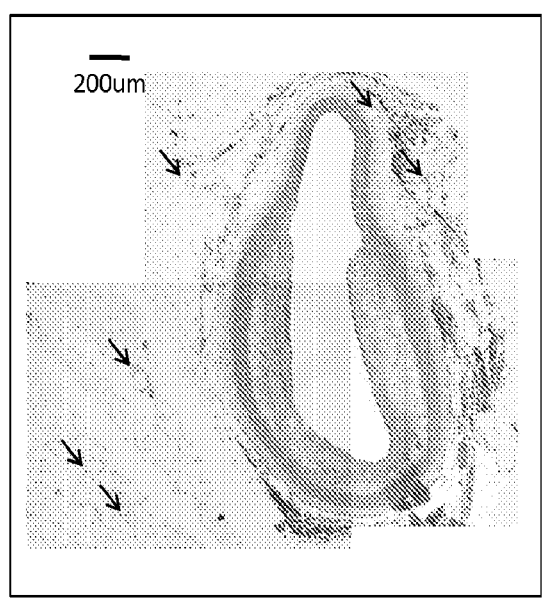
FIG. 20 illustrates a cross-sectional view of plaque formed in the abdominal aorta of a rabbit 12 weeks after undergoing endothelial denudation, including 5 weeks of a high-fat high-cholesterol diet. An eccentric plaque and microvessels (arrows) can be seen in the H&E stained histological slide.

FIG. 19 illustrates IVUS B-mode and RM images of citrated blood (top) and MB (bottom) circulated at a mean velocity of 20 cm/s (150 mL/min) in a 4 mm wall-less 2% (w/w) agar tissue mimicking phantom containing scatterers (20 μm Sigmacell, Sigma-Aldrich), with the catheter rotating at 30 Hz. Blood and tissue signals are significantly cancelled out while MB signal in enhanced in the RM images. Yellow dots are separated by 1 mm. The dark circle in the center is the space occupied by the transducer. Dynamic ranges are respectively 40 dB and 30 dB for the B-mode and RM-mode images.

In FIG. 19, it can be seen that increasing the blood velocity to 20 cm/s and the imaging frame rate to 30 Hz only marginally deteriorated tissue suppression. The very short interval between the pair of pulses directly accounts for that. In more detail, it can be calculated that in a 14 μs span, blood cells traveling at 20 cm/s have traveled 2.8 μm, which is 2 orders of magnitude below the 25 MHz elevation and lateral resolution (200 μm range). Similarly, in 14 us, at 2 mm and 30 Hz frame rate, the IVUS HF beam has only moved 5.3 μm. Notably, the delay could be further shortened by a factor 2 since only 5 mm in depth are required. Using a 220 mVpp LF excitation voltage pullback image sequences at native IVUS frame rate of 30 frames per second could be acquired without inducing catheter deterioration.

The embodiments disclosed herein (e.g., FIG. 13) also illustrate that a sub-population of MBs in the 3.5-4.5 μm size range contributed mostly to the RM signal, with a synchronization phase for resonance ($\pi/2$ and $3\pi/2$). This corresponds to ~38% of the MBs in our MB population, between 3.5 and 4.5 μm in size (e.g., FIG. 9). This estimation is corroborated by the appearance of the RM images (FIGS. 18 and 19), which are patchy with bright areas surrounded by darker areas with very little RM signal, whereas the corresponding B-mode images are more uniform. Considering a normal MB size distribution and the $3\pi/2$ delay RM response from the disclosed embodiments, we estimated the effect of narrower MB size dispersion on the RM signal, by calculating the size-weighted integral of the RM for MBs with decreasing size dispersion. It was found that for a mean MB size of 4 μm, a 3 dB increase in RM signal can be expected by decreasing the standard deviation of the MB population from 1.3 to 0.5 and a 4 dB increase with further decrease to 0.1 μm. These projections are in agreement with the ~38% MB response estimated earlier, based on a linear RM superposition assumption. There are different approaches for decreasing microbubble size dispersion, including micro-fluidic flow focusing devices and differential centrifugation techniques. Successive differential centrifugation steps can be used to generate a monodispersed MB population with size distribution of 4.2±0.1, precisely in the size range delineated in some of the embodiments disclosed herein.

Radiation force can improve MB adhesion by pushing MB closer to the wall for molecular imaging. We have observed that microbubbles were pushed away from the catheter by the RM pulse complexes, which was not observed with only HF pulses. The large radiating pattern of the LF pulse and high line density (320 pulses per frame) can account for this observation. Examining the simulations results in FIG. 13, it can be seen that a HF/LF synchronization of π and 2π result in a positive or negative RM signal polarity depending on a MB size larger or smaller than resonance. Numerical studies predict that the natural resonance frequency of MB oscillating in a constrained environment can increase of decrease depending on the surrounding tissue rigidity and compliance. If there is a change in the resonance frequency of targeted versus non targeted-MB, as suggested by these simulations studies, RM imaging could be used to differentiate targeted from non targeted MB, and allow a direct, specific imaging of targeted-MB, by monitoring the polarity of the signal. IVUS RM imaging could be used to push MB to the wall and image adhered MB in molecular imaging.

As described above, the embodiments disclosed herein provide for the performance of radial modulation approaches for contrast specific high resolution IVUS imaging using a single element catheter. Simulations and in vitro characterization in a mock flow phantom indicate that by driving MB near resonance, it is possible to achieve a $CTR_{RM}$ of 12.0±0.9 dB and a CTRI of 14.2±1.8 dB at 2 mm. Both parameters decreased to 5.1±0.6 and 3.0±0.7 dB at 5 mm, which is sufficient penetration for coronary imaging. Microvessels embedded in scattering tissue and perfused with MB where masked in B-mode could be readily resolved in RM-mode. Blood circulating at coronary flow rates was also cancelled out. The data indicates that RM imaging performance can benefit from using monodispersed MB. Radiation force pushing MB away from the catheter was observed, and can be used for molecular imaging. Using a different synchronization phase (above or below resonance), RM imaging can be used to differentiate targeted from non-targeted MB if targeting induces a change in MB resonance frequency.

Example 3

In Vivo Testing

In Vivo Testing.

The IVUS system was tested in the abdominal aorta of a hyper cholesterolemic rabbit.

Rabbit Model.

The New Zealand male white rabbits (3 to 4 kg) were fed a high fat (4.5%) and high cholesterol (0.5%) diet for 5 weeks starting 1 week prior to entry into the study. Rabbits were anesthetized using ketamine (40 mg/kg IM) and xylazine (5 mg/kg IM) and maintained on 2.5% isoflurane. A Fogarty balloon was then introduced percutaneously into the femoral artery and advanced under fluoroscopic guidance into the abdominal aorta. The balloon was inflated and advanced and retracted 3 times between lumbar vertebrae L2 and L4 to denude the endothelium distally to the renal bifurcations. The catheter was removed and the animal was allowed to recover. 12 weeks later, the animal was similarly anaesthetized for imaging. After imaging, animals was euthanized by increasing Isoflurane to 5% for 5 minutes, followed by an injection of a supersaturated solution of pharmaceutical grade potassium chloride and perfusion fixed.

In Vivo Imaging.

The injured section of the abdominal aorta was inspected for plaque presence using contrast fluoroscopy and a conventional B-mode IVUS imaging (40 MHz) pullback. A section bearing plaque was chosen for imaging using the RM IVUS system.

Figure 21:
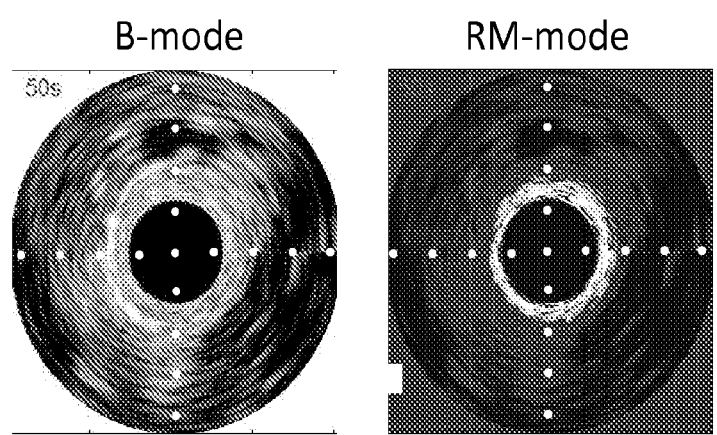
FIG. 21 illustrates a typical IVUS B-mode (left) and RM-mode (right) image acquired in vivo in the abdominal aorta of a rabbit with 12 week old plaque after the systemic injection of microbubbles. MBs fill the lumen around the IVUS catheter and appear very bright in the RM image whereas they are about as bright as tissue in the B-mode image.
Figure 22:
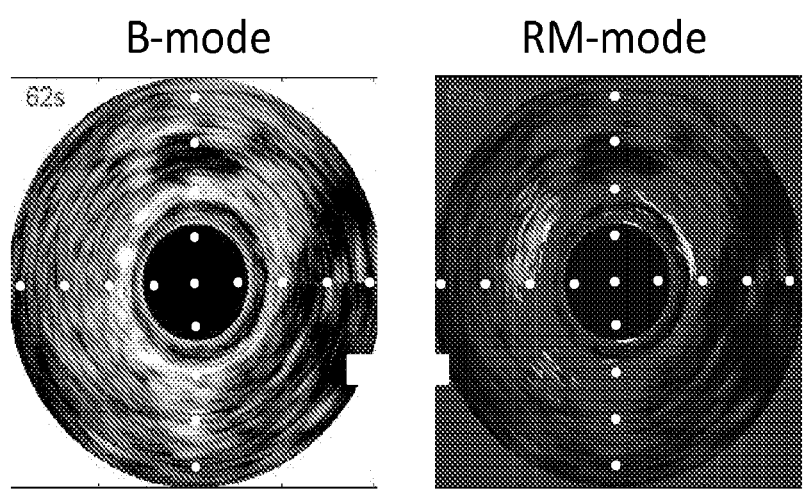
FIG. 22 illustrates the same IVUS B-mode (left) and RM-mode (right) image as in the previous figure, after flushing the MB from the vessel lumen using an inflated angioplasty balloon positioned upstream of the catheter. Vena cava (10 o'clock), branching vessel (7 o'clock) and MB on the aortic wall are now hyper echoic in the RM image.

RM imaging was performed before and after flushing MB from the lumen. This was achieved by positioning an angioplasty balloon 2 cm upstream of the IVUS imaging plane and covering the renal arteries. After infusing 1 ml of lipid encapsulated MB ($1\times10^9$ MB/ml) using an ear vein, RM frame were acquired before and after inflating the balloon to occlude the flow while flushing 5 mL of saline. Typical B-mode and RM-mode images before (FIG. 21) and after (FIG. 22) flushing the MB from the lumen are shown in FIGS. 21 and 22.

Flushing the MB from the lumen allowed to decrease the attenuation from MB in the lumen while a high concentration MB was still flowing in the other vessels. MB in the vena cava and in a branching vessel can be seen in the RM frame of FIG. 22 whereas they are masked by the MB in the lumen in FIG. 21.

Accordingly, the methods and apparatuses described herein allow high spatial resolution imaging with a contrast agent designed for much lower frequencies. The catheter-type design allows automatic alignment of the two ultrasound beams. The custom waveforms can be tailored to the acoustic property of the microbubbles. The IVUS system allows the ultrasound pulses to be adjusted based on the particular microbubble-based agent used. Using these apparatuses, very low concentration of microbubbles and signal bubbles can be imaged. This capability can be particularly useful, for example, in targeted microbubble images for the detection of vasa vasorum and for the characterization of atherosclerotic plaques.

Finally, it should be noted that various MBs can be used in the manner described herein. In some embodiments, molecular imaging of plaque components using MBs targeted to adhere to plaque specific epitopes (adhesion molecules, macrophages, MMPs) can further improve the capabilities of risk stratifying individual lesions.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of imaging a blood vessel, the method comprising:
    delivering a bubble-based contrast agent within the vessel;
    positioning at least one ultrasound device in the vicinity of the bubble-based contrast agent within the vessel;
    delivering a first burst of ultrasound energy directed at the bubble-based contrast agent to excite the bubble-based contrast agent, the first burst of energy comprising a first low-frequency component and a first high-frequency component, the first high-frequency component and the first low-frequency component having a first relative timing, the first high-frequency component being delivered while the bubble-based contrast agent is being exited by the first low-frequency component;
    delivering a second burst of ultrasound energy directed at the excited bubble-based contrast agent, the second burst of energy comprising a second low-frequency component and a second high-frequency component, the second high-frequency component and the second low-frequency component having a second relative timing the second high-frequency component being delivered while the bubble-based contrast agent is being exited by the second low-frequency component;

receiving one or more return signals from the high-frequency ultrasound energy of the first and second bursts; and processing the one or more return signals to obtain a first image of the excited bubble-based contrast agent, wherein the first and second relative timings are different, the low-frequency components have a frequency of less than 5 MHz, and the high-frequency components have a frequency of greater than 15 MHz.

2. The method of claim 1, wherein the low-frequency components have a frequency of between 1 and 5 MHz and the high-frequency components have a frequency of between 15 and 50 MHz.

3. The method of claim 1, wherein the processing of the one or more return signals to obtain the first image comprises processing the one or more return signals to reduce the portions of the one or more return signals that correspond to one or more portions of a surface within the vessel.

4. The method of claim 1, wherein the processing of the one or more return signals further comprises forming a second image, the second image corresponding to one or more portions of a surface within the vessel.

5. The method of claim 1, wherein the method includes delivering a plurality of frames of first and second bursts.

6. The method of claim 5, wherein a center frequency of the first and second bursts can be adjusted during the method of imaging to accommodate different resonance frequencies of the bubble-based contrast agent.

7. The method of claim 5, wherein a time period between respective first burst and the second burst in the frames can be adjusted during the method of imaging.

8. The method of claim 7, wherein the first and second relative timings can be adjusted between a first phase arrangement where the second burst of a frame is temporally located at the positive going zero-crossing of the first burst of the same frame and a second phase arrangement where the second burst of a different frame is temporally located at the negative going zero-crossing of the first burst of the different frame.

9. The method of claim 7, wherein the first and second relative timings can be adjusted between a third period where the second burst of a frame is temporally located at the maximum of the first burst and a fourth period where the second burst of a different frame is temporally located at the minimum of the first burst of the different frame.

10. The method of claim 1, wherein the at least one ultrasound device is coupled to a distal end portion of a catheter, the catheter comprising an elongate tubular body.

11. The method of claim 1, wherein the at least one ultrasound device is a pair of concentric ultrasound elements, the pair of concentric ultrasound elements comprising an outer ultrasound element configured to deliver the first burst of low-frequency ultrasound energy and an inner ultrasound element configured to deliver the second burst of high-frequency ultrasound energy.

12. The method of claim 1, wherein the at least one ultrasound device is a pair of adjacent ultrasound elements, the pair of adjacent ultrasound elements comprising a first ultrasound element configured to deliver the first burst of low-frequency ultrasound energy and a second ultrasound element configured to deliver the second burst of high-frequency ultrasound energy.

13. The method of claim 1, wherein the at least one ultrasound device comprises a single ultrasound element capable of delivering the first and second bursts of ultrasound energy.

14. The method of claim 1, wherein the at least one ultrasound device comprises an array of ultrasound elements, the array comprising a plurality of first ultrasound elements configured to deliver the first burst of low-frequency ultrasound energy and a plurality of second ultrasound elements configured to deliver the second burst of high-frequency ultrasound energy.

15. The method of claim 1, wherein the catheter further comprising an injection portion, the injection port being configured to allow for the delivery of the bubble-based contrast agent within the vessel.

16. The method of claim 1, wherein the bubble-based contrast agent comprises lipid encapsulated microbubbles.

17. The method of claim 1, further comprising moving the at least one ultrasound device within the vessel to form a three-dimensional reconstruction of the vessel.

18. The method of claim 17, further comprising analyzing the three-dimensional reconstruction to identify features associated with plaque formation within the vessel to establish a clinical diagnosis.

* * * * *

UNITED STATES PATENT AND TRADEMARK OFFICE
CERTIFICATE OF CORRECTION

PATENT NO. : 9,603,582 B2
APPLICATION NO. : 14/241051
DATED : March 28, 2017
INVENTOR(S) : Chen et al.

Page 1 of 1

It is certified that error appears in the above-identified patent and that said Letters Patent is hereby corrected as shown below:

In the Claims

Column 20, Line 60, Claim 1 "exited" should read – excited –

Column 21, Line 2, Claim 1 "exited" should read – excited –

Signed and Sealed this
Thirtieth Day of January, 2018

Joseph Matal
*Performing the Functions and Duties of the
Under Secretary of Commerce for Intellectual Property and
Director of the United States Patent and Trademark Office*